United States Patent
Ma et al.

(10) Patent No.: US 6,281,257 B1
(45) Date of Patent: Aug. 28, 2001

(54) POROUS COMPOSITE MATERIALS

(75) Inventors: Peter X. Ma; Ruiyun Zhang, both of Ann Arbor, MI (US)

(73) Assignee: The Regents of the University of Michigan, MI (US)

( * ) Notice: Subject to any disclaimer, the term of this patent is extended or adjusted under 35 U.S.C. 154(b) by 0 days.

(21) Appl. No.: 09/292,896

(22) Filed: Apr. 16, 1999

Related U.S. Application Data

(60) Provisional application No. 60/083,196, filed on Apr. 27, 1998.

(51) Int. Cl.⁷ .................................. C08J 9/26; C08J 9/28
(52) U.S. Cl. ............................. 521/61; 521/64; 424/43; 424/78.3; 424/426; 424/428
(58) Field of Search ............................. 521/61; 424/426, 424/428, 43, 78.3

(56) References Cited

U.S. PATENT DOCUMENTS 5,102,983 * 4/1992 Kennedy ............................... 528/354
5,686,091 * 11/1997 Leone et al. ......................... 264/45.6

FOREIGN PATENT DOCUMENTS

52485 * 2/1998 (JP) .

OTHER PUBLICATIONS

Abstract of JP10–052,485A2, CA:248:6181 Chem Abstrcts, Feb. 2, 1998.*
Abe, Y. et al., Apatite Coating On Ceramics, Metals, and Polymers Utilizing A Biological Process. *J. Mater. Sci.: Mater. Med.*, vol. 1, pp. 233–238 (1990).
Akao, M. et al., "Mechanical properties of sintered hydroxyapatite for prosthetic application," *J. Materials Science* 16:809–812 (1981).
Akao, M. et al., "In vitro mineralization in bovine tooth germ cell cultured with sintered hydroxyapatite," *J. Materials Science: Materials in Medicine* 4:569–574 (1993).
Breur, C. et al., "Tissue Engineering Lamb Heart Valve Leaflets," *Biotechnology and Bioengineering* 50:562–567 (1996).
Cao, Y. et al., "Tissue Engineering of Tendon," in *Ploymers in Medicine and Pharmacy*, A.G. Mikos, et al., Editors 1995, MRS: Pittsburgh 394:83–89.
Flahiff, C. et al., "Analysis of a biodegradable composite for bone healing," *J. Biomedical Materials Research* 32:419–424 (1996).
Kim, T. et al., "Enhanced Survival of Transgenic Hepatocytes Expressing Hepatocyte Growth Factor in Hepatocyte Tissue Engineering," *Transplant Proc.*, 29(1–2):858–860 (1997).
Kitsugi, T. et al., "Bone bonding behavior of $MgO-CaO-SiO_2-P_2O_5-CaF_2$ glass (mother glass of A–W–glass–ceramics)," *J. Biomedical Materials Research* 23:631–648 (1989).
Kokubo, T. et al., "Solutions able to reproduce in vivo surface–structure changes in bioactive glass–ceramic $A-W^3$," *J. Biomedical Materials Research* 24:721–734 (1990).
Kokubo, T. et al., Ca, P–Rich Layer Formed On High–Strength Bioactive Glass Ceramic A–W. *J. Biomed. Mater. Res.*, vol. 24, pp. 331–343 (1990).
Langer, R. et al., "Tissue Engineering," *Science* 260:920–926 (1993).
Li, P. et al., Apatite Formation Induced By Silica Gel In A Simulated Body Fluid. *J. Am. Ceram. Soc.*, vol. 75, pp. 2094–2097 (1992).
Li, P., et al., In Vitro Calcium Phosphate Formation Induced By Sol–Gel–Prepared Silica. *J. Biomed. Mater. Res.*, vol. 29, pp. 325–328 (1995).
Lo, H. et al., "Fabrication of Controlled Release Biodgradable Foams by Phase Separation," *Tissue Engineering* 1(1):15–28 (1995).
Ma, P. et al., "Degradation, Structure and Properties of Fibrous Nonwoven Poly(Glycolic Acid) Scaffolds for Tissue Engineering," in *Polymers in Medicine and Pharmacy*, A.G. Mikos, et al., Editors 1995, MRS: Pittsburgh 394 :99–104.
Ma, P. et al., "Development of Biomechanical properties and morphogenesis of in vitro tissue engineered cartilage," *J. Biomed Mater Res*, 29(12):1587–1595 (1995).
Ma, P. et al., "Fabrication of Biodegradable Polymer Foams for Cell Transplantation and Tissue Engineering," in *Tissue Engineering*, M.Yarmush and J. Morgan, Editors. 1998, Humana Press Inc.: Totowa, NJ.
Ma, P. et al., "Biodegradable woven/nonwoven composite scaffolds for pulmonary artery engineering in an juvenile lamb model," *Transaction of the Society for Biomaterials* pp. 295 (1997).
Mikos, A. et al., "Preparation and characterization of poly(L–lactic acid) foams," *Polymer* 35(5):1068–1077 (1994).
Nerem, R. et al., "Tissue Engineering: From Biology to Biological Substitutes," *Tissue Engineering* 1(1):3–13 (1995).
Puleo, D. et al., "Osteoblast responses to orthopedic implant materials in vitro," *J. Biomedical Materials Research* 25:711–723 (1991).
Rehman, I. et al., "Characterization of hydroxyapatite and carbonated apatite by photo acoustic FTIR spectroscopy,"; *J. Materials Science: Materials in Medicine* 8:1–4 (1997).

(List continued on next page.)

Primary Examiner—Morton Foelak
(74) Attorney, Agent, or Firm—Medlen & Carroll, LLP

(57) ABSTRACT

Methods and compositions are described that provide three dimensional porous matrices as structural templates for cells. The porous matrices of the present invention have desirable mechanical properties suitable to a variety of applications, including platforms for in vitro cell cultivation, implants for tissue and organ engineering, and materials suitable for chromatography and filtration.

21 Claims, 25 Drawing Sheets

OTHER PUBLICATIONS

Schugens, C. et al., "Polyactide macroporous biodegradable implants for cell transplanatation. II. Preparation of polylactide foams by liquid–liquid phase separation," *J. Biomedical Materials Research* 30:449–461 (1996).

Shinoka, T. et al., "Tissue–Engineered Heart Valve Leaflets. Does Cell Origin Affect Outcome?," *Circulation* 96(9 Suppl):II–102–107 (1997).

Shinoka, T. et al., "Tissue–engineered heart valves. Autologous valve leaflet replacement study in a lamb model," *Circulation* 94(9 Suppl):II–164–168 (1996).

Shinoka, T. et al., "Tissue–Engineering Heart Valves: Valve Leaflet Replacement Study in a Lamb Model," *Annals of Thoracic Surgery* 60(6 Suppl):S513–516 (1995).

Shinoka, T. et al., "Creation of Viable Pulmonary Artery Autografts through Tissue Engineering," *J. Thoracic & Cardiovascular Surgery* 115(3):536–545 (1998).

Tretinnikov, O. N., et al., In Vitro Hydroxyapatite Deposition Onto A Film Surface–Grafted With Organophosphate Polymer. *J. Biomed. Mater. Res.*, vol. 28, pp. 1365 –1373 (1994).

Verheyen, C. et al., "Evaluation of hydroxylapatite/poly (L–lactide) composites: physico–chemical properties," *J. Materials Science: Materials in Medicine* 4:58–65 (1993).

Whinnery, L. et al., "Engineering the Macrostructure of Thermally Induced Phase Separated Polysilane Foamsm," *J. Polymer Science: Part A: Polymer Chemistry* 34:1623–1627 (1996).

Zund, G. et al., "The in vitro construction of a tissue engineered bioprosthetic heart valve," *Eur J Cardiothorac Surg* 11(3):493–497 (1997).

\* cited by examiner

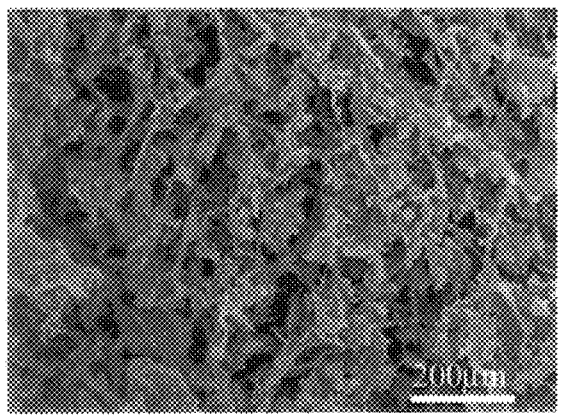
A
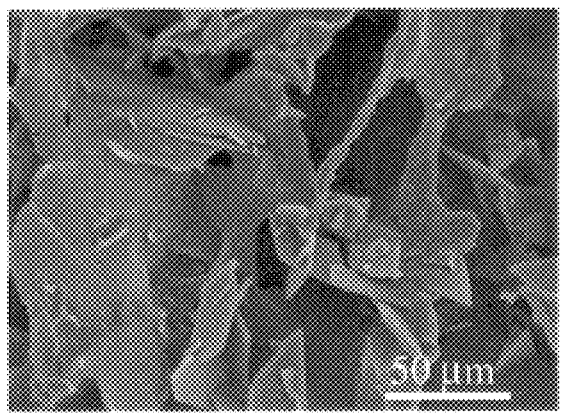
B
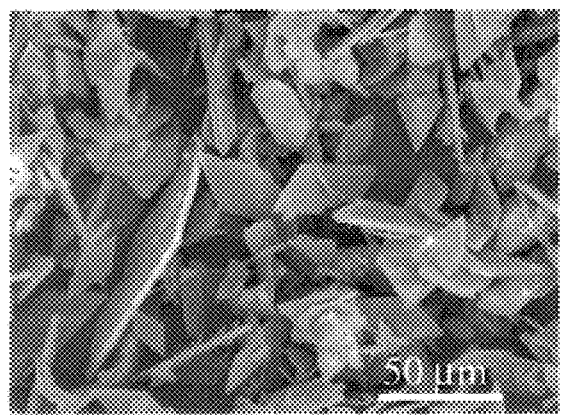
C
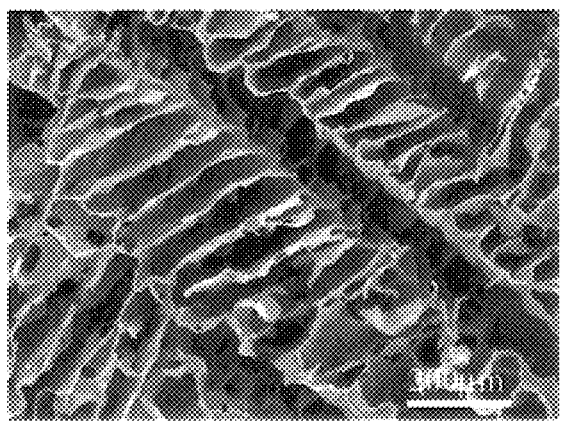
D
FIG. 1

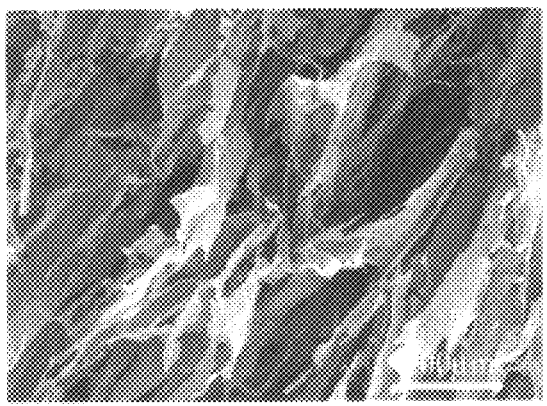
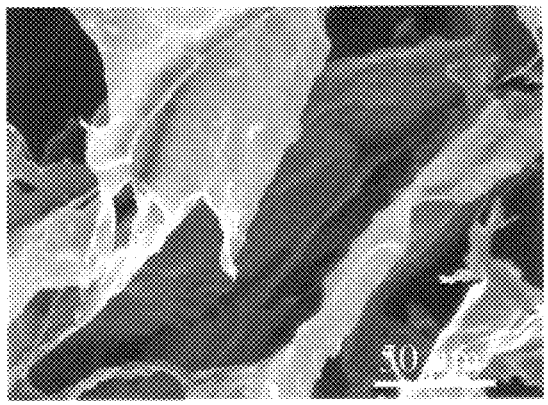
A
B
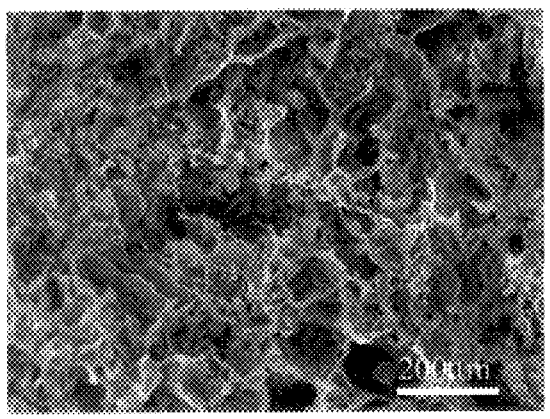
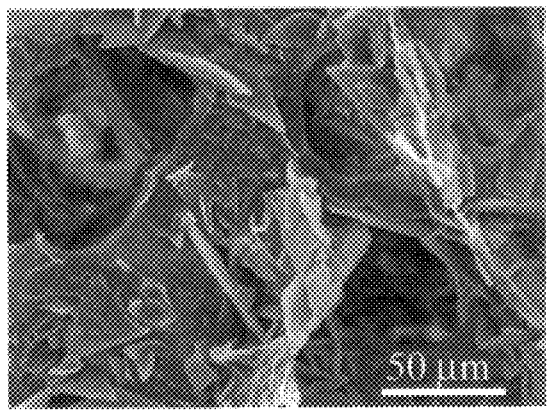
C
D
FIG. 2

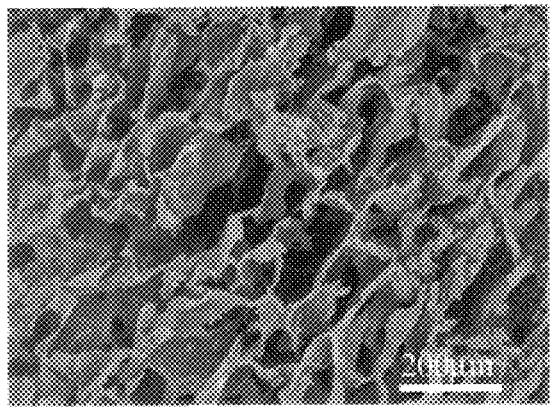 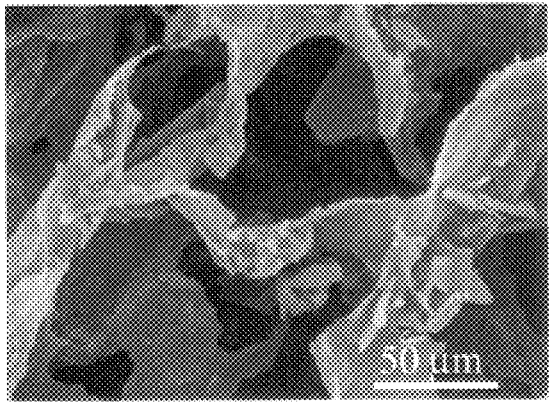
A  B
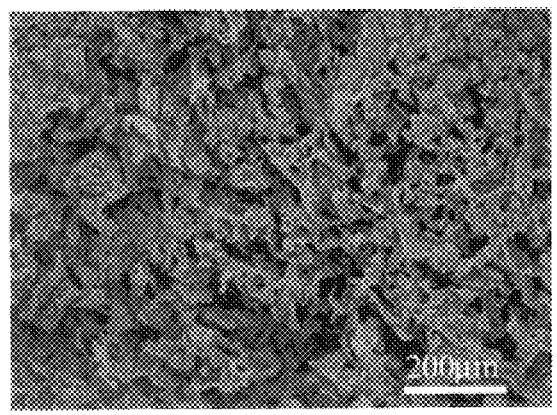 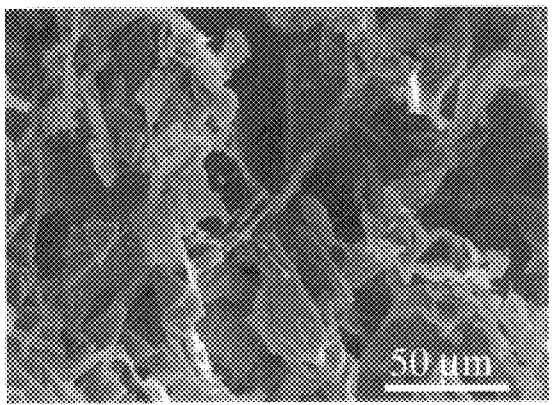
C  D
FIG. 3

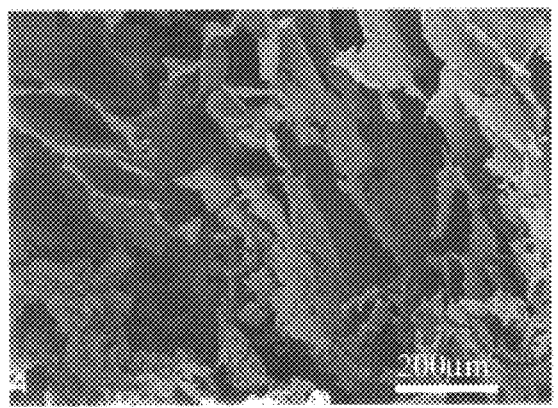
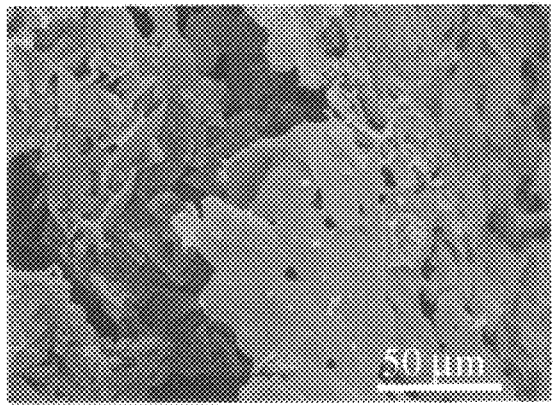
A
B
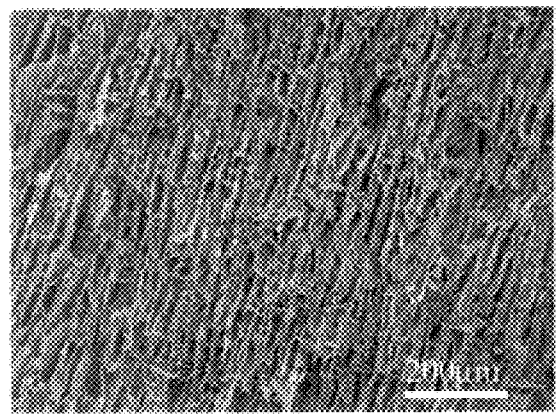
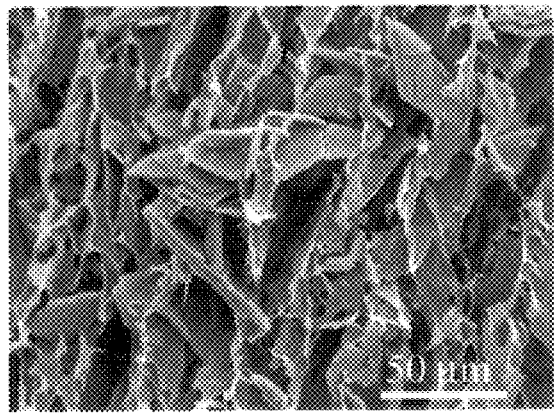
C
D
FIG. 4

ION CONCENTRATIONS OF VARIOUS SIMULATED BODY FLUIDS AND HUMAN BLOOD PLASMA

| | pH | Na | K | Ca | Mg | Cl | $HCO_3$ | $HPO_4$ | $SO_4$ |
|---|---|---|---|---|---|---|---|---|---|
| | | | | | ION CONCENTRATION (mM) | | | | |
| HUMAN PLASMA | 7.4 | 142.0 | 5.0 | 2.5 | 1.5 | 103.0 | 27.0 | 1.0 | 0.5 |

FIG. 5

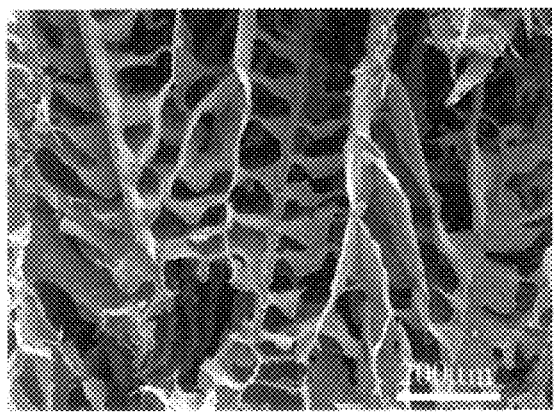
A
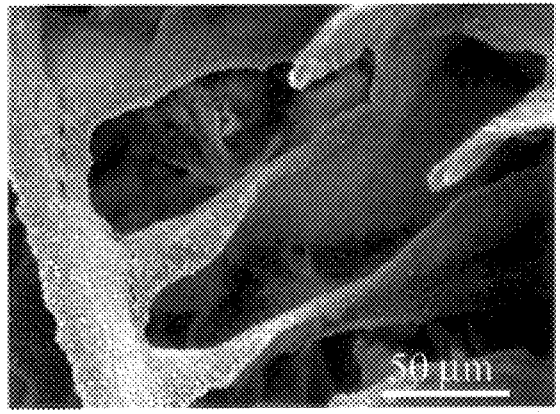
B
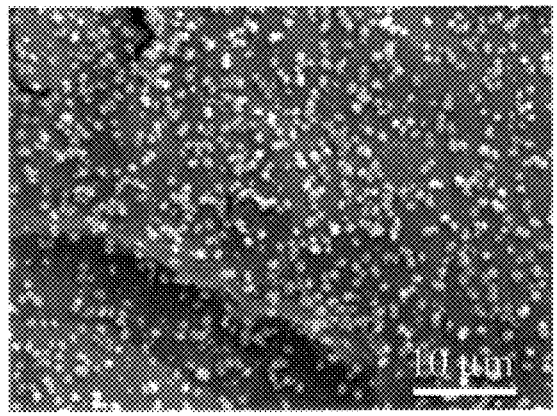
C
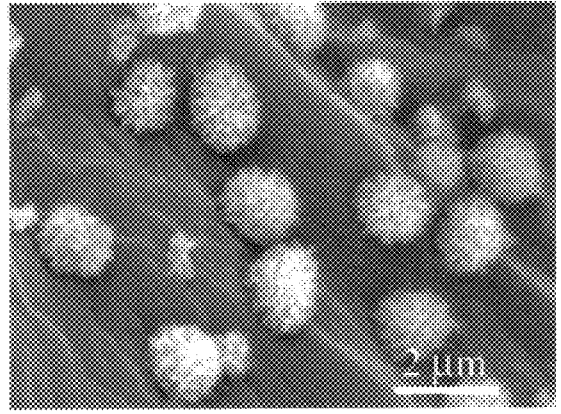
D
FIG. 6

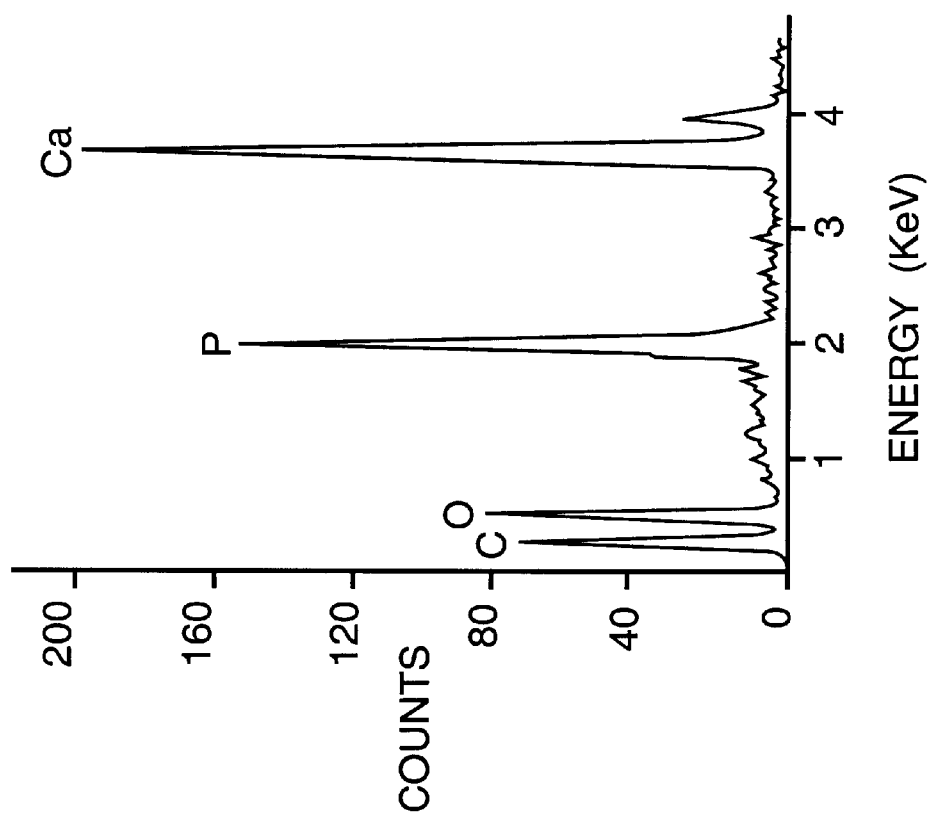
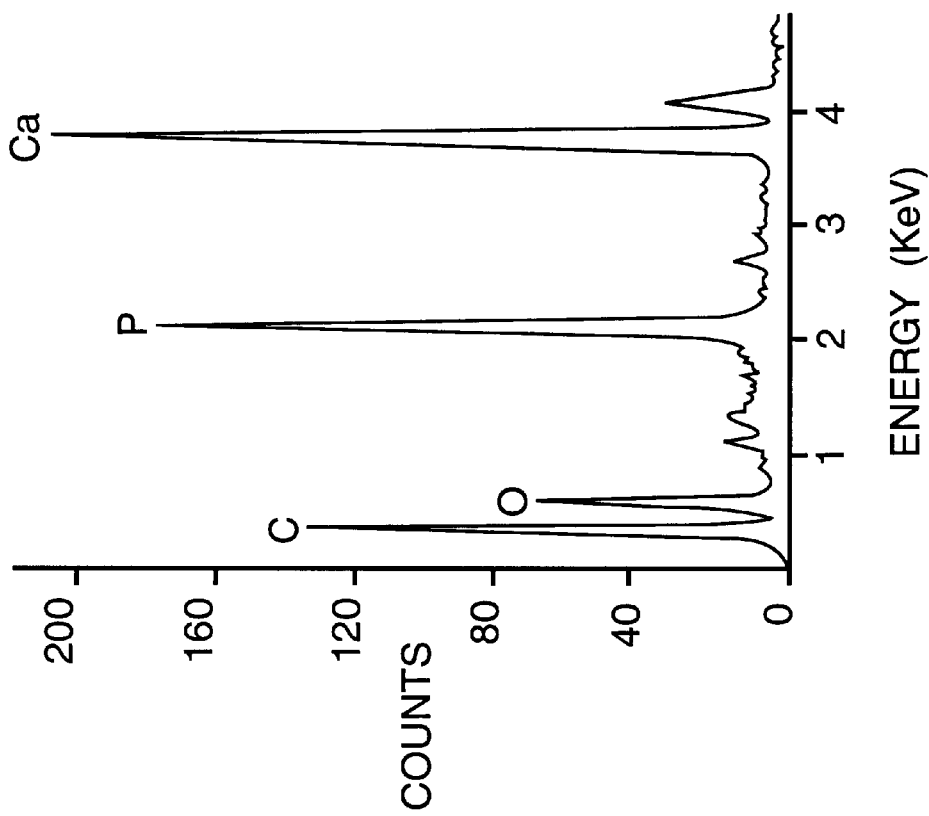

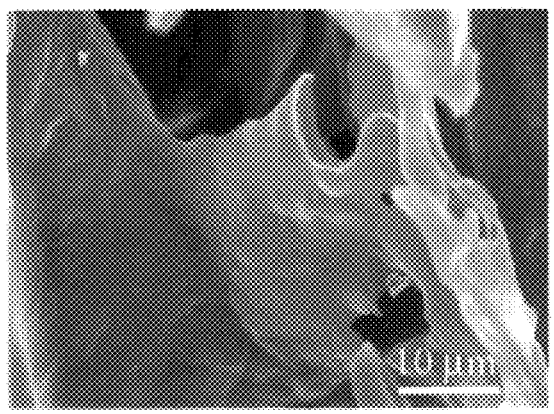 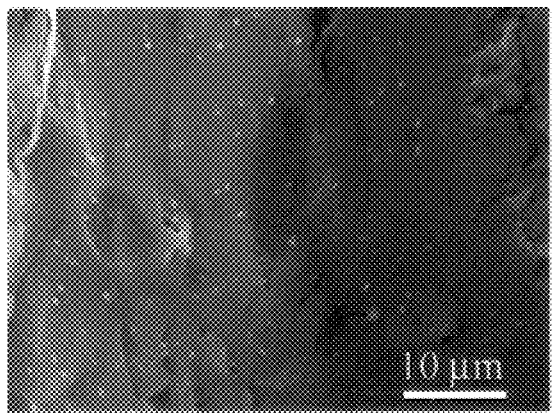
A  B
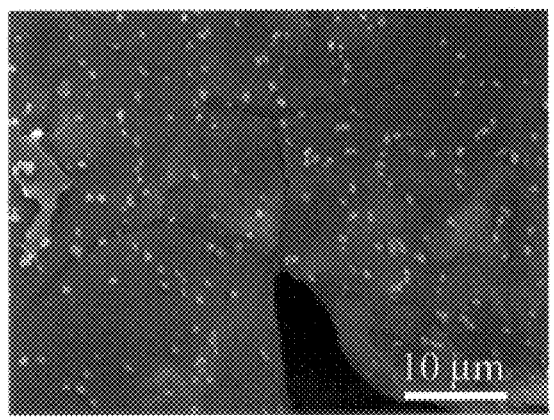 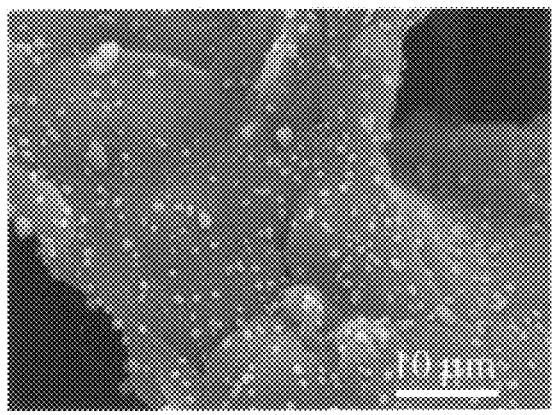
C  D
FIG. 10

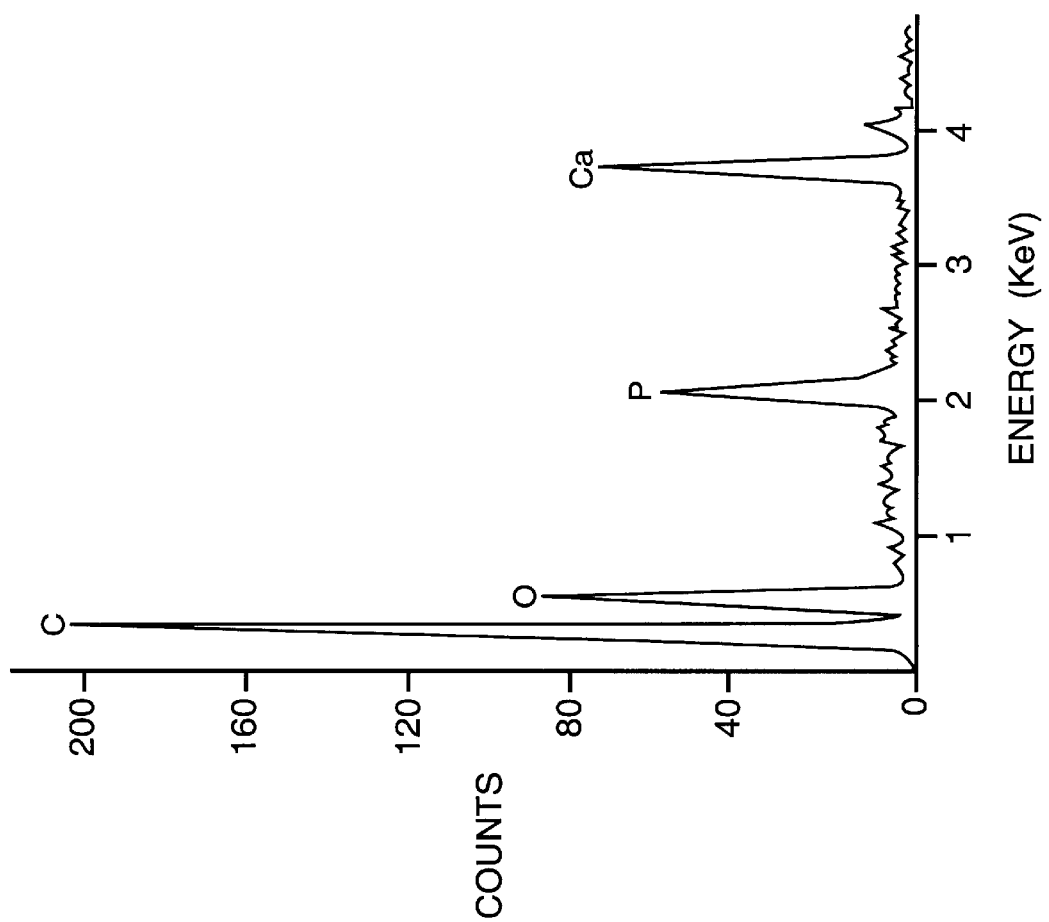

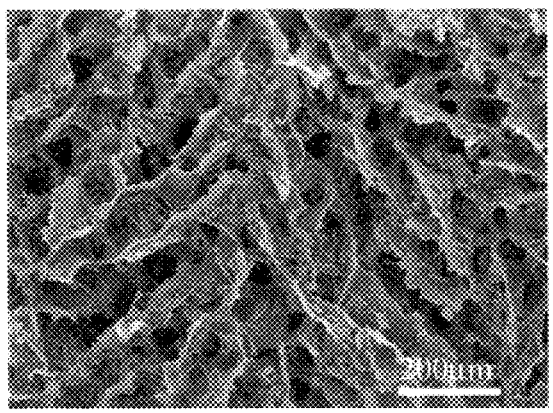 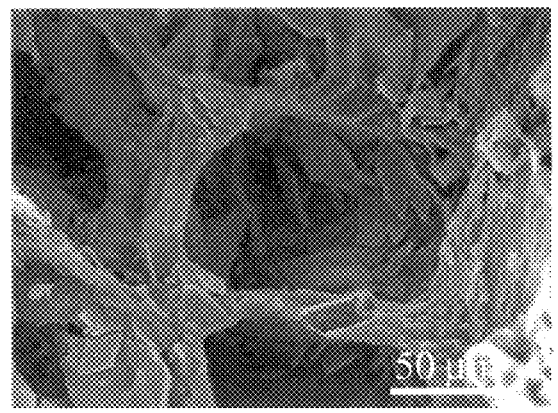
A        B
FIG. 14

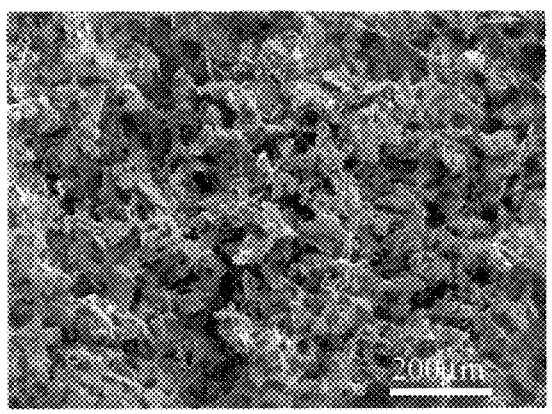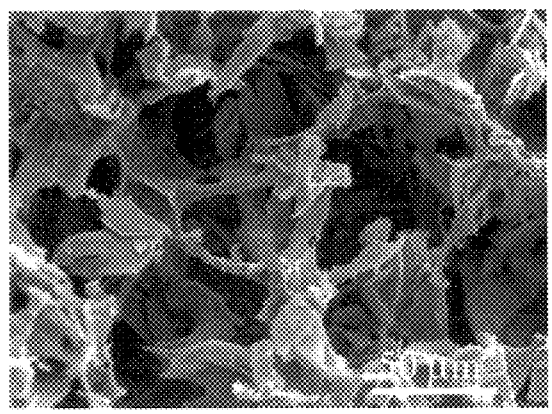
A	B
FIG. 15

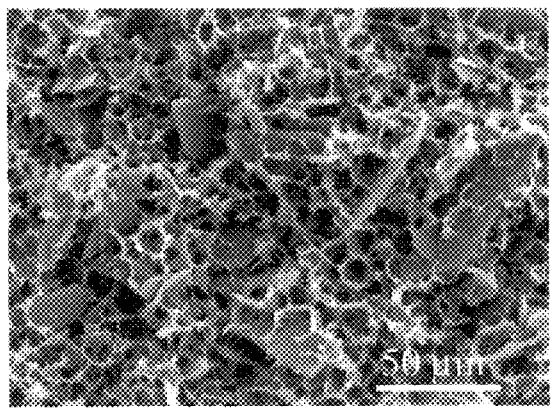 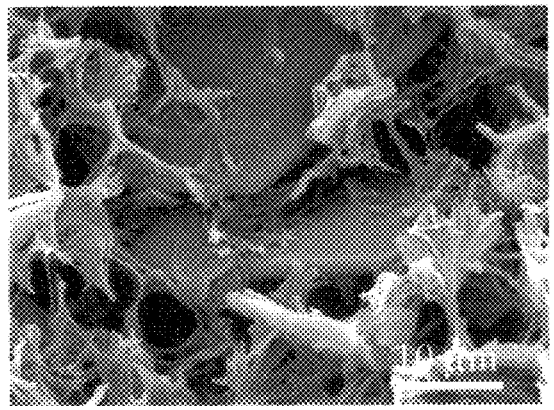
A B
FIG. 16

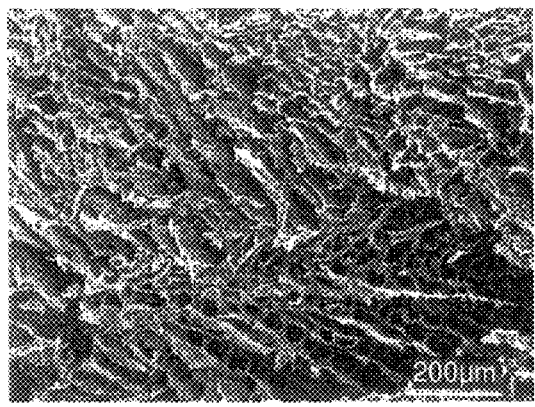 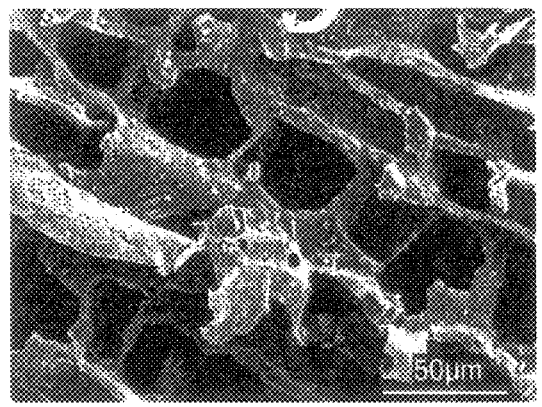
A          B
FIG. 23

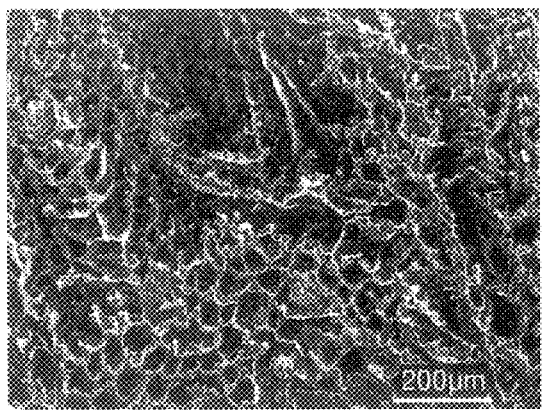 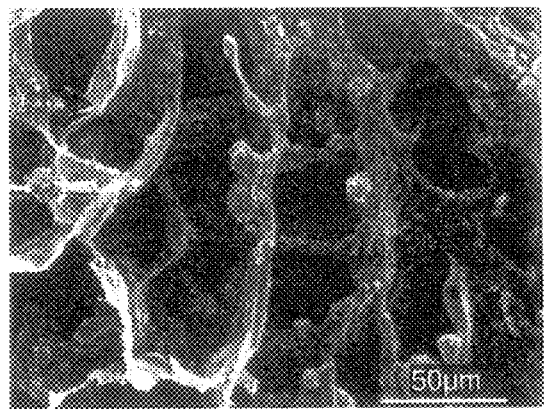
A                                B
FIG. 24

POROUS COMPOSITE MATERIALS

This application claims priority to a Provisional Application—Ser. No. 60/083,196 filed Apr. 27, 1998.

FIELD OF THE INVENTION

The present invention relates to methods of synthesis for porous composite materials as well as the resulting porous composite materials as compositions suitable as a matrix for cellular infiltration and ingrowth, and in particular, the cultivation of cells within said matrix for the fabrication and repair of tissues and organs. In addition, said porous composite material has applications in chromatography, filtration, vibration absorption, insulation, and biodegradable packaging materials.

BACKGROUND

Transplantation is a life-saving therapy but is seriously limited by the scarcity of donor organs. In contrast to native tissue and organ transplantation from a non-autologous donor, tissues and organs generated through tissue engineering provide a more abundant alternative source for highly sought after biological materials. Scaffolding plays a pivotal role in the engineering of new tissues and organs. Various tissues have been engineered from highly porous scaffolds prepared from synthetic biodegradable polymers such as poly(glycolic acid), poly(lactic acid), and poly(glycolic acid-co-lactic acid). Alginic acid, a polysaccharide from seaweeds, is a family of natural copolymers of b-D-mannuronic acid and a-L-guluronic acid. Because of their biocompatibility, abundance in source, and low prices, they have been widely used in food industry as thickeners and emulsifying agents. They have also been processed into gel beads encapsulating living cells as an means of immunoprotection. However, alginate is difficult to work with because of its mechanical properties. What is needed is a matrix, readily fashioned into a given shape, having a desired porosity.

In addition, the passage of a fluidic mixture across a porous matrix facilitates the resolution of compounds contained within said mixture. Irregular pore size within a given matrix, however, can impair the separation of compounds of said mixture. What is needed is a matrix, readily fashioned into a given shape, having a desired porosity.

SUMMARY OF THE INVENTION

The present invention relates to methods of synthesis for porous composite materials as well as the resulting porous composite materials as compositions suitable as a matrix for cellular infiltration and ingrowth, and in particular, the cultivation of cells within said matrix for the fabrication and repair of tissues and organs. In one embodiment, the present invention contemplates a method wherein a matrix of a composite material comprising a desired porosity is used as a three dimensional structural template for in vitro tissue engineering applications. In another embodiment, the present invention contemplates a method wherein a matrix of an implantable composite material, comprising a desired porosity, is used as a three dimensional structural template facilitating the infiltration of cells in vivo. In addition, said porous composite material has applications in chromatography and filtration.

In a specific embodiment, the present invention contemplates a method comprising: a) providing: i) a polymer source, ii) an inorganic compound, and iii) a solvent; b) mixing said polymer with said solvent to create a homogenous polymer solution; c) adding said inorganic compound to said homogenous polymer solution to create a mixture; d) subjecting said mixture to such conditions whereby a solvent free matrix of a desired porosity (e.g. greater than approximately 80%, more preferably in greater than approximately 85%, still more preferably greater than approximately 90%, and most preferably greater than approximately 95%) is created. While the above-named components can be reacted in an alternative order, the above referenced reaction sequence has been found to produce the best results.

In a preferred embodiment, the present invention contemplates a method, comprising: a) providing: i) a polymer source, ii) an inorganic compound, and iii) a solvent; b) mixing said polymer with said solvent to create a polymer solution; c) adding said inorganic compound to said polymer solution to create a mixture; d) freezing said solvent in said mixture to create a frozen mixture; e) treating said frozen mixture (i.e. the mixture comprising frozen solvent) under conditions whereby a solvent free matrix is created having a porosity greater than approximately 80%. A variety of treatments in step e) are contemplated including but not limited to freeze drying to remove said solvent.

As noted above, the present invention specifically contemplates the resulting porous composite materials as compositions. In one embodiment, the present invention contemplates a composition comprising at least one polymer and at least one inorganic compound, said composition having a desired porosity (e.g. greater than approximately 80%, more preferably greater than approximately 85%, still more preferably greater than approximately 90%, and most preferably greater than approximately 95%).

In another embodiment, the present invention contemplates a method comprising: a) providing: i) a polymer source, ii) a solvent, and iii) a simulated body fluid; b) mixing said polymer with said solvent to create a homogenous polymer solution; c) subjecting said mixture to such conditions whereby a solvent free matrix of a desired porosity is created; d) contacting said solvent free matrix with said simulated body fluid.

In another embodiment, the present invention contemplates a method comprising: a) providing: i) a matrix of a desired porosity and ii) a simulated body fluid; and b) contacting said matrix with said simulated body fluid.

It is not intended the present invention be limited to a particular polymer or polymer source. The present invention contemplates homopolymers, copolymers and/or a mixture of polymers. In one embodiment, the polymer source is poly(L-lactic acid) (PLLA). In another embodiment, the polymer is poly(D,L-lactic acid-co-glycolic acid (PLGA). In another embodiment, the polymer is poly(methyl methacrylate) (PMMA). In another embodiment, the polymer is polystyrene (PS). These above referenced polymers are available from a variety of commercial vendors including Boehringer Ingelheim (Ingelheim, Germany) and from Medisorb Technologies International L. P. (Cincinnati, Ohio). Additionally, these polymers are used without further purification.

It is not intended the present invention be limited to a specific inorganic compounds used in the second phase of the above described methods. In one embodiment, the inorganic compound used is hydroxyapatite (HAP). In another embodiment, the inorganic compound is calcium phosphate (CAP). In another embodiment the inorganic compound is glass powder (GP).

Finally, it is also not intended that the present invention be limited to a specific solvent. In one embodiment the solvent is dioxane. In one embodiment the solvent is a mixture of dioxane and water. In another embodiment the solvent is benzene. In another embodiment the solvent is a mixture of benzene and chloroform.

The present invention also contemplates the use of a three dimensional matrix as a composition. Moreover, the present invention contemplates the using three dimensional matrices in combination with other components, such as cells. Where cells are used, it is not intended that the present invention be limited to a specific cell type (e.g. one cell type infiltrating a matrix). A variety of cell types (including mixtures of different cells) are contemplated. In one embodiment, the cells are osteoblasts. In another embodiment the cells are fibroblasts. In another embodiment the cells are epithelial. In another embodiment, the cells secrete a medically useful compound (e.g., hormone, cytokine, etc.). Such cells may be (but need not be) cells that have been manipulated by recombinant means to secrete such compounds.

The present invention contemplates methods wherein cells are added and grown in and on the matrix, as well as methods wherein the matrix is implanted (both with and without cells).

The present invention also contemplates methods wherein some of the matrices biodegrade, in vivo and in vitro, subsequent to the confluent growth of cells in and on the matrix. The present invention also contemplates methods wherein some of the matrices are not biodegradable.

As noted above, the porous composite materials of the present invention have a number of applications, including chromatography, filtration, vibration absorption, insulation, and biodegradable packaging materials. For example, the present invention contemplates the resulting composite materials suitable as a matrix for chromatography and filtration. In one embodiment, the matrix is fashioned into a column suitable for the resolution of molecules in a fluid. In another embodiment the porous matrix is cast into a filter suitable for the sequestration of molecules from a fluid.

DEFINITIONS

To facilitate understanding of the invention, a number of terms are defined below.

The present invention contemplates implanting a matrix into hosts. The term "host" refers to both humans and animals.

A "matrix" refers to a three dimensional support for cells which divide free space into partially enclosed domains which remain in fluidic communication with adjacent domains.

"Porosity" is represented as a percentage derived from the equation: $V_p/V \times 100$, wherein $V_p$ is defined as the total volume of pores in a specimen and V is equal to the total volume of the specimen.

An "inorganic compound" is defined as a substance which does not have carbon. Preferred inorganic compounds are materials comprising ceramics and glass. Ceramics are non-metallic heterogeneous materials that are strong, brittle, and resistant to heat and attack by chemicals. Glass, in contrast, is homogeneous noncrystalline "frozen solution" that may be melted and remelted as often as desired.

"Metastable" is defined as a substance having a narrow margin of stability such as a supersaturated solution.

"Biodegradable" refers to a material capable of being broken down into readily metabolized compounds by the action of living beings such as cells in vitro or in vivo.

As used herein, the term "implant" and "implanting" and the like indicates placement on, in, or through a patient's body (including placement in body cavities) in the course of medical treatment, e.g., for a disease, impairment or injury. Implants include, but are not limited to, implants for wound care, drug delivery, and bone replacement.

"Simulated Body Fluid" refers to a man-made aqueous solution comprising calcium and phosphorous ions at concentrations in a range between 0.5–2.5 times the concentration of said ions found in normal human plasma. For use in the present invention, it is preferred that elements in the simulated body fluid will not precipitate unless contact is made with a structure or surface.

"Solvent Free" refers to a composite polymer/inorganic compound matrix wherein the interstices of said matrix are substantially free from residual solvent such that said matrix reaches a constant mass upon sublimation. By "substantially free" it is meant that, with normal detection means (such as detection by changes in mass), no solvent is detected. While it is believed that the methods of the present invention yield a matrix that is completely free of solvent, it is possible that some solvent remains detectable in extremely small amounts by extreme detection methods (e.g. detection methods with extremely high resolution).

"Quenching" refers to the cooling rate of a solution.

DESCRIPTION OF THE DRAWINGS

FIG. 1 shows Scanning Electron Micrographs (SEMs) of (a) PLLA/HAP, (b) PLLA/HAP, (c) PLLA matrices and (d) HAP particles at different magnifications (100×, 500×, 500× and 100×, respectively).

FIG. 2 shows SEMs of PLLA/HAP matrices prepared from mixtures with PLLA/dioxane concentrations (wt/v) of (a) 1.0%, (b) 1.0%, (c) 7.5% and (d) 7.5% at different magnifications (100×, 500×, 100× and 500×, respectively).

FIG. 3 shows SEMs of PLLA/HAP matrices prepared from PLLA/HAP/dioxane mixtures with HAP contents of (a) PLLA/HAP=70/30, (b) PLLA/HAP=70/30, (c) PLLA/HAP=30/70 and (d) PLLA/HAP=30/70 at different magnifications (100×, 500×, 100× and 500×, respectively).

FIG. 4 shows SEMs of PLLA/HAP matrices prepared by quenching temperatures of (a) 8° C., (b) 8° C., (c) Liquid nitrogen and (d) Liquid nitrogen at different magnifications (100×, 500×, 100× and 500×, respectively).

FIG. 5 presents average molar values for the concentration of ions in human plasma.

FIG. 6 shows SEMs of a PLLA matrix incubated in SBF for 30 days at different magnifications: (a) 100× (b) 500× (c) 2,000× and (d) 10,000.

FIG. 7 presents an energy-dispersive spectra (EDS) of microparticles from (a) PLLA matrix incubated in SBF for 30 days and (b) PLLA film incubated in SBF for 15 days.

FIG. 10 presents SEMs, at 2,000× magnification, of a PLLA matrix incubated in SBF for different periods of time: (a) 3 days, (b) 6 days, (c) 10 days, and (d) 15 days.

Figure 13:
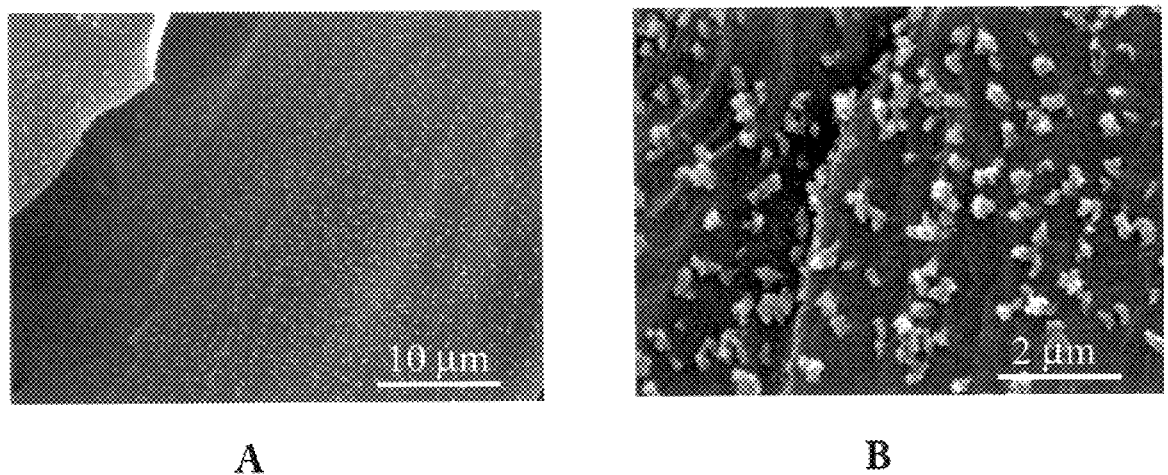

FIG. 13 presents SEMs of a PLLA matrix immersed in $H_2O$, at 37° C., for 15 days and subsequently incubated in SBF, at different magnifications: (a) 2,000× and (b) 10,000×.

FIG. 14 presents SEMs of a PLLA/HAP matrix prepared from a mixture of HAP with a PLLA/dioxane solution at a polymer concentrations of 5.0 (wt/v)% to yield a matrix of PLLA/HAP=50/50 at different magnifications: (a) 100× and (b) 500×.

FIG. 15 presents SEMs of a [PLGA=(75/25)]/HAP matrix prepared from the mixture of HAP with a [PLGA=(75/25)]/dioxane solution at a polymer concentration of 2.5 (wt/v)% to yield a matrix of PLGA/HAP=50/50 at different magnifications: (a) 100× and (b) 500×.

FIG. 16 presents SEMs of a PLLA/HAP matrix prepared from the mixture of HAP with a PLLA/[dioxane and $H_2O$=(90/100)] solution at a polymer concentration of 5.0 (wt/v)% to yield a matrix of PLLA/HAP=50/50 at different magnifications: (a) 100× and (b) 500×.

Figure 17:
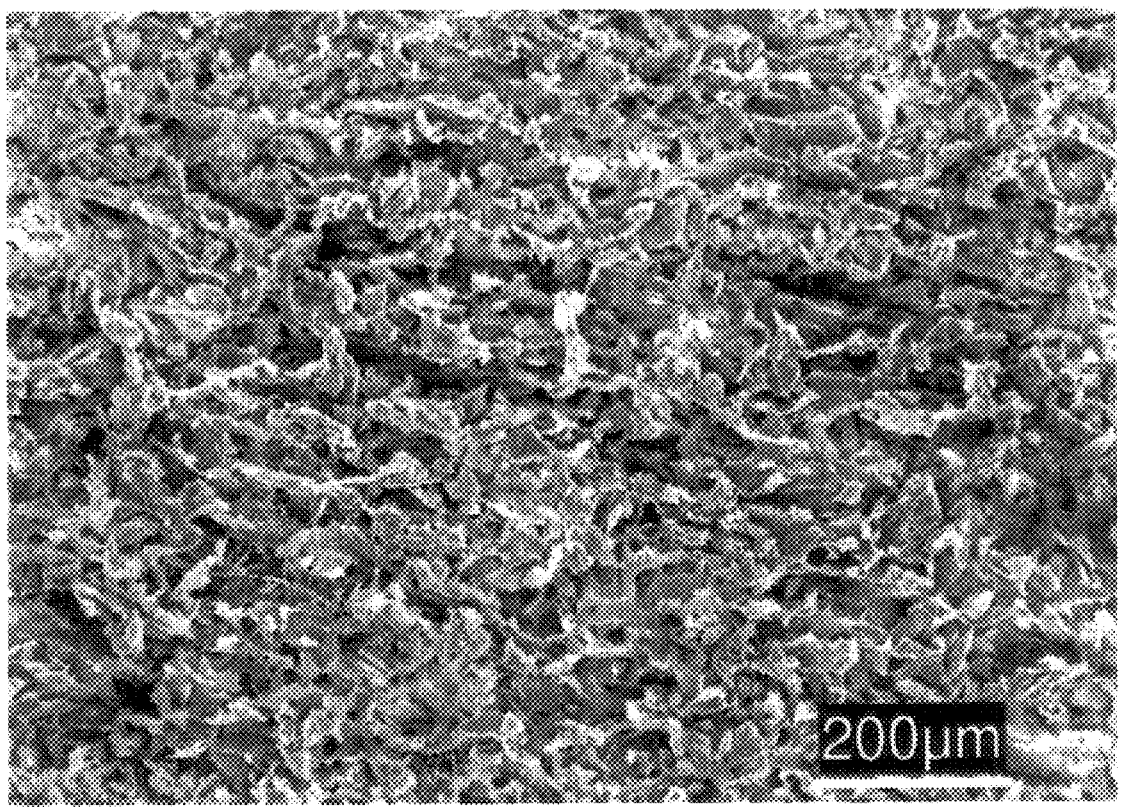

FIG. 17 presents an SEM micrograph, at 100× magnification, of a PLLA/HAP matrix prepared from the mixture HAP with a PLLA/benzene solution at a polymer concentration of 5.0 (wt/v)%.

Figure 18:
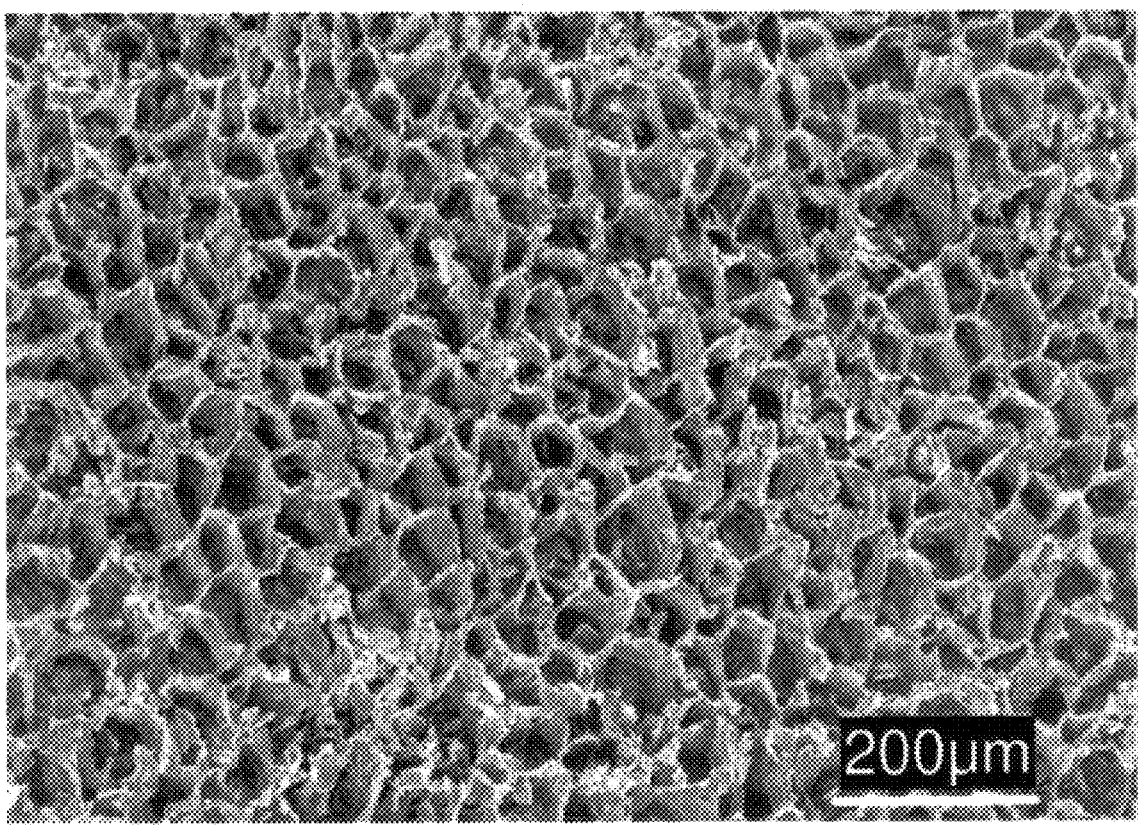

FIG. 18 presents an SEM micrograph, at 100× magnification, of a [PLGA (75/25)]/HAP matrix prepared from the mixture of HAP with a PPLA/benzene solution at a polymer concentration of 5.0 (wt/v)%.

Figure 19:
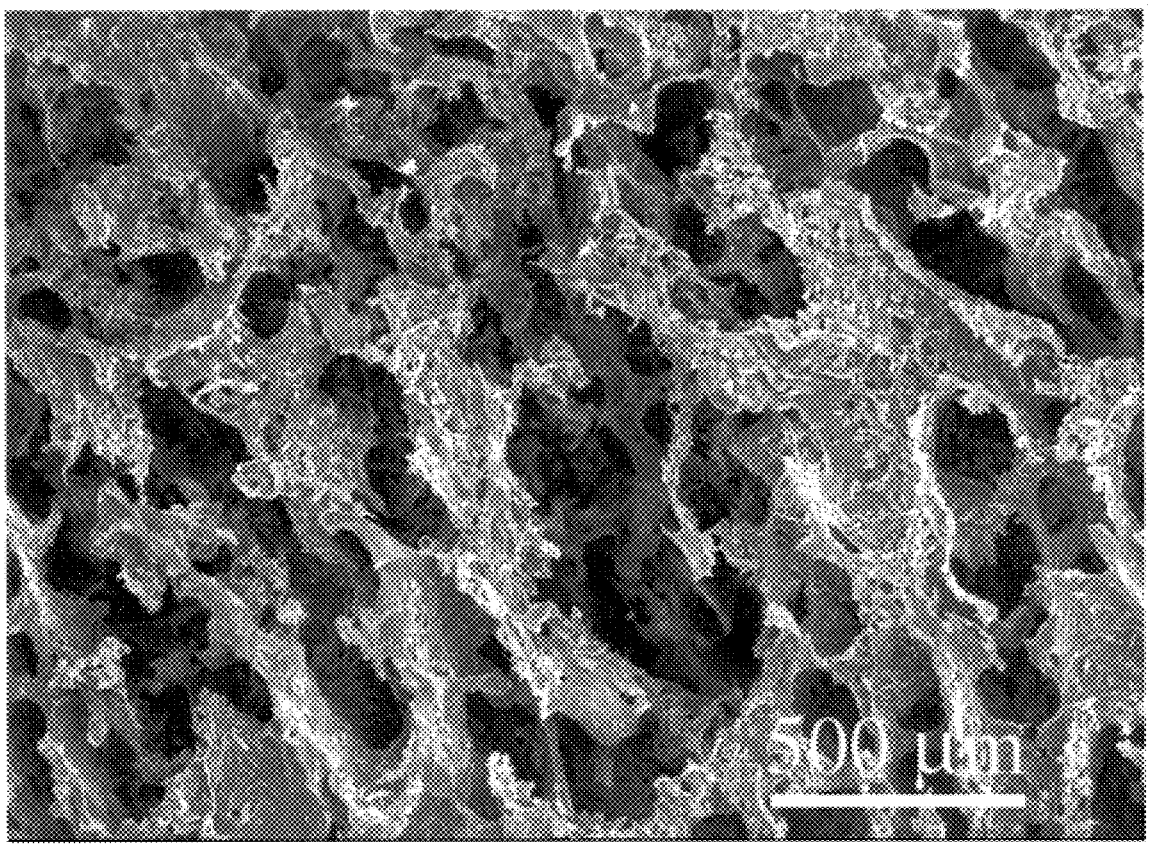

FIG. 19 presents an SEM micrograph, at 50 ×, of a PLLA/HAP matrix prepared from the mixture of HAP with a PLLA/[benzene/chloroform 90/10)] solution at a polymer concentration of 5.0 (wt/v)%.

Figure 20:
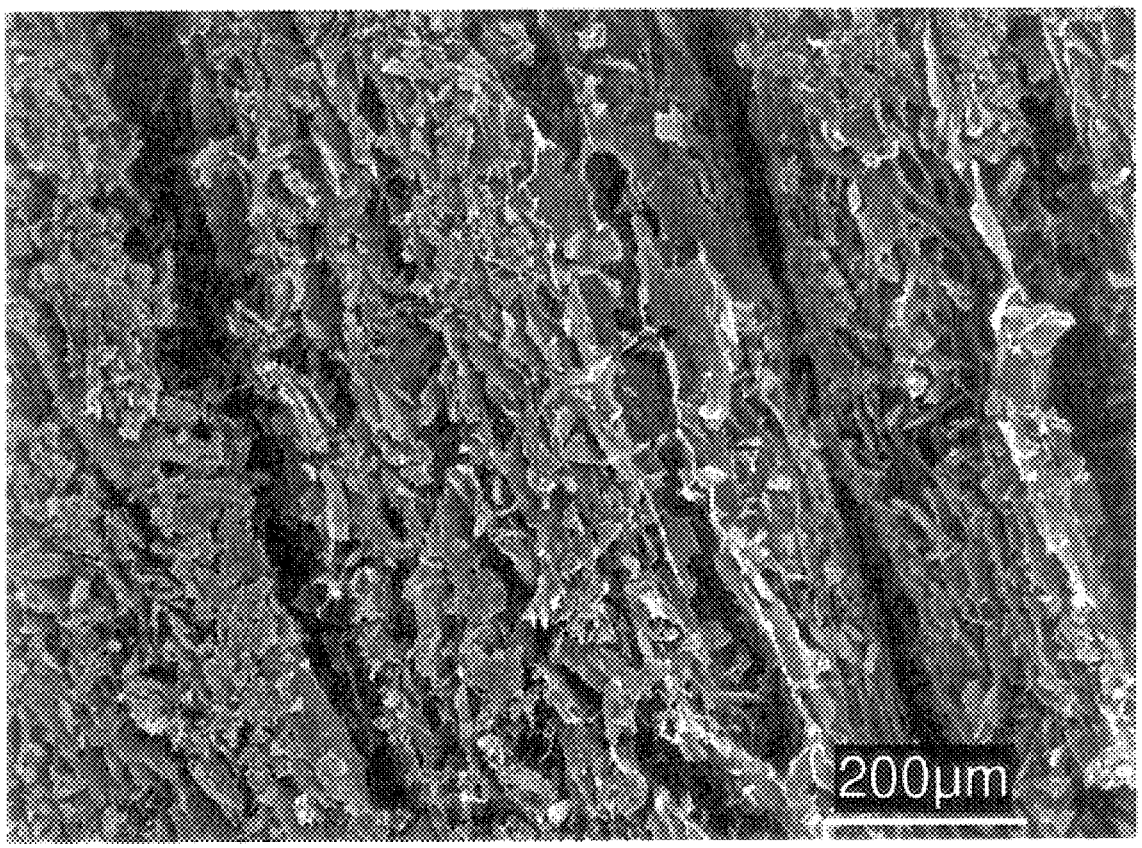

FIG. 20 presents an SEM micrograph, at 100× magnification, of a PMMA/HAP matrix prepared from the mixture of HAP with a PMMA/dioxane solution at a polymer concentration of 5.0 (wt/v)%.

Figure 21:
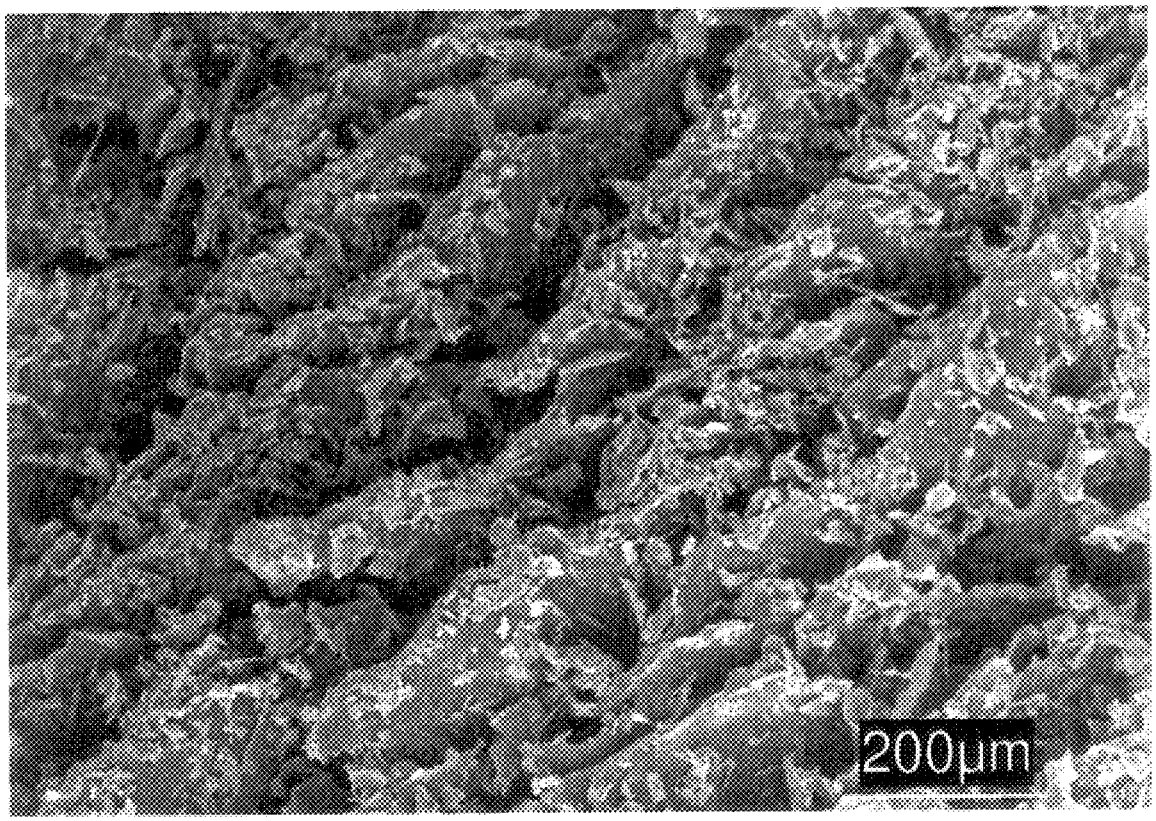

FIG. 21 presents an SEM micrograph, at 100× magnification, of a [PMMA-MAA (80/20)]/HAP matrix prepared from the mixture of HAP with a PMMA-MAA (80/20)/dioxane solution at a polymer concentration of 5.0 (wt/v)%.

Figure 22:
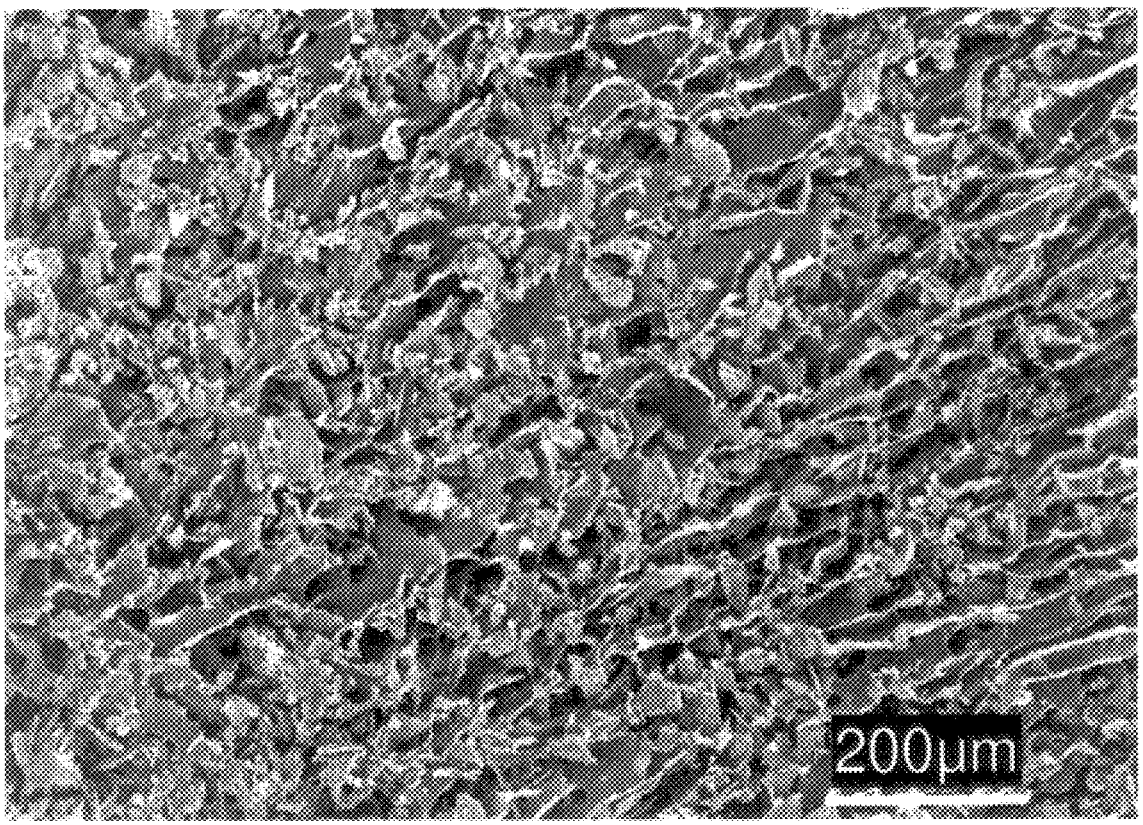

FIG. 22 presents an SEM micrograph, at 100× magnification, of a PS/HAP matrix prepared from the mixture of HAP with a PS/dioxane solution at a polymer concentration of 5.0 (wt/v)%.

FIG. 23 presents an SEM micrograph of a PLLA/CAP matrix prepared from the mixture of CAP with a PLLA/dioxane solution at a polymer concentration of 5.0 (wt/v)% at different magnifications: (a) 100× and (b) 500×.

FIG. 24 presents an SEM micrograph of a PLLA/GP matrix prepared from the mixture of GP with a PLLA/GP/dioxane solution at a polymer concentration of 5.0 (wt/v)% at different magnifications: (a) 100× and (b) 500×.

DESCRIPTION OF THE INVENTION

The present invention relates to methods of synthesis of porous composite materials and the resulting porous composite materials as compositions suitable as a matrix for cellular infiltration, and in particular, the cultivation of cells within said matrix for the fabrication and repair of tissues and organs. In addition, said porous composite material has applications in chromatography and filtration. The present invention demonstrates that a variety of polymer sources, inorganic compounds, and solvents may be used to construct a matrix with a desired porosity. The microstructure of said pores can be controlled by varying the type of polymer, polymer concentration, inorganic compound content, quenching temperature, and solvent utilized. The present invention also provides a method for contacting matrices with simulated body fluid such that bonding of hydroxyapatite, onto the exposed surfaces of said matrix, is favored.

Living cells may be incorporated into the matrices and cultured in vitro. In the alternative, the matrix may be maintained in an in vitro tissue culture environment. Depending on the selection of polymer source and inorganic compounds, a biodegradable matrix may be created. Such a biodegradable matrices form a structural template that may be resorbed by infiltrating cells. These variations illustrate how a composite three dimensional matrix with a desired porosity may be used as an tissue engineering template. Given the availability of the material sources and relative ease in processing said materials into the instant porous matrices, the instant three dimensional matrix is well suited to large-scale tissue engineering and manufacture.

Experimental

The following examples serve to illustrate certain preferred embodiments and aspects of the present invention and are not to be construed as limiting the scope thereof.

I. Materials

The following compounds are used as polymer sources. Poly(L-lactic acid) with an inherent viscosity of approximately 1.6 is available from Boehringer Ingelheim (Ingelheim, Germany). Poly(D,L-lactic acid-co-glycolic acid) (75/25) with inherent viscosity of 0.5~0.65 is available from Medisorb Technologies International L. P. (Cincinnati, Ohio). Poly(methyl methacrylate) (PMMA) with an average molecular weight of 350,000 is available from Aldrich (Aldrich Chemical Company, Inc., Milwaukee, Wis.). Poly (methyl methacrylate-co-methacrlic acid (80/20) is available from Polysciences, Inc. (Warrington, Pa.). Polystyrene is available from Aldrich Chemical Company (Milwaukee, Wis.). These polymers are used without further purification.

Hydroxyapatite ($3Ca_3(PO_4)_2 \cdot Ca(OH)_2$) (HAP), available from Aldrich Chemical Company (Milwaukee, Wis.), Calcium phosphate $CaHO_4P$ (CAP), and glass powder ($SiO.Al_2O_3.CaF_2$) (GP) are obtained from and are used as inorganic second phase compounds.

The following compounds are used as solvents: dioxane, a mixture of dioxane and water, benzene, a mixture of benzene and chloroform. The organic solvents are obtained from Aldrich Chemical Company (Milwaukee, Wis.).

II. Methods

A. Porous Polymer/Inorganic Second Phase Matrix Fabrication

1. Preparation of Polymer/Inorganic Second Phase Mixture

The polymer source is weighed into a flask, and then an accurately measured amount of solvent is added into the flask to make a solution with a desired concentration (from 1 (wt/v)% to 7.5 (wt/v)%). The mixture is stirred at 50° C. for two hours to obtain a homogeneous polymer solution. An inorganic compound is added into the prepared solution to make a polymer/inorganic second phase mixture. The final composition of a polymer/inorganic second phase composite matrix is determined by the concentration of the polymer solution and inorganic second phase content in the mixture.

2. Polymer/Inorganic Second Phase Matrix Formation

The Polymer/Inorganic second phase matrix is prepared by solid-liquid phase separation and subsequent sublimation of the solvent. While the instant invention is not limited to reagents employed in the following example; a typically matrix is prepared according to the following steps. 10 ml of PLLA/HAP/dioxane mixture is added into a beaker (30 ml, prewarmed to 50° C.). The beaker containing the mixture is rapidly transferred into a refrigerator or a freezer at a preset temperature, equal to or lower than the melting point of said solvent, to solidify the solvent and induce solid-liquid phase separation. The solidified mixture is maintained at that temperature for 2 hours and then immersed into liquid nitrogen to deep freeze the mixture. The frozen mixture is transferred into a freeze-drying vessel at a temperature between −5° C. and −10° C. in an ice/salt bath. The samples are freeze-dried at 0.5 mmHg for four days to completely remove the solvent. The solvent free matrices are stored in a desiccator.

3. Matrix Characterization

The density and porosity of a matrix is measured by liquid displacement. A matrix sample of weight W is immersed in a graduated cylinder containing a known volume (VI) of ethanol. The sample is kept in the ethanol for 5 minutes and then a series of brief evacuation-repressurization cycles are conducted to force the ethanol into pores of the matrix. Cycling is continued until no air bubbles are observed emerging from the matrix. The total volume of ethanol and the ethanol-impregnated matrix is then recorded as $V_2$. The volume difference, $(V_2-V_1)$, is the volume of the polymer/inorganic second phase composite skeleton of the matrix. The ethanol impregnated matrix is removed from the cylinder and then the residual ethanol volume is recorded as $V_3$. The quantity $(V_1 V_3)$, the volume of the ethanol held in the matrix, is determined as the void volume of the matrix, thus the total volume of the matrix is $V=(V_2-V_1)+(V_1-V_3)=V_2-V_3$. The density of the matrix, d, is expressed as:

$$d=W/(V_2-V_3)$$

and, the porosity of the matrix, e, is obtained by:

$$e=(V_1-V_3)/(V_2-V_3)$$

The porous morphologies of the composite matrices are studied by scanning electron microscopy (SEM) (S-3200N, Hitachi, Japen) at 15 KV. The specimens are cut with a razor blade after being frozen in liquid nitrogen for 5 minutes, and then are coated with gold using a sputter coater (Desk-II, Denton Vacuum Inc). The gas pressure is less than 50 mtorr and the current is about 40 mA. The coating time is 200 seconds.

A typical SEM micrographs of the PLLA/HAP composite matrix prepared from 2.5 (wt/v)% PLLA solution with a quenching temperature of −18 ° C. shows co-continuous structure of interconnected irregular pores and a polymer/HAP composite skeleton (FIG. 1a). The irregular pores range from several microns up to about 300 microns. The walls of the pores are composed of both PLLA and HAP (FIG. 1b). The HAP platelets ranging from 10 to 100 mm in size (FIG. 1c) are randomly distributed in the PLLA matrix.

The morphology of this PLLA/HAP matrix is much different from pure PLLA matrix, at 100x, (FIG. 1d) prepared with the same procedure. The PLLA matrix prepared from solid-liquid phase separation of the PLLA/dioxane solution [from 2.5 (wt/v)% PLLA/dioxane solution (quenched to −18° C.)] has a highly anisotropic tubular morphology with an internal ladder-like structure.

To study the effect of polymer concentration on the matrix structure, a series of polymer/inorganic second phase composite matrices prepared using, but not limited to, an exemplar model of PLLA/HAP/dioxane mixtures with PLLA concentration ranging from 1.0 (wt/V)% to 7.5 (wt/v)%.

In this model, the ratio of PLLA to HAP is kept at one. The composite matrix made from 1.0 (wt/v)% PLLA solution is composed of bonded very thin PLLA leaflets (FIGS. 2a and 2b). Almost all the HAP particles precipitate at the bottom of the sample, presumably due to the low viscosity of the PLLA solution. The matrices prepared from 5.0% and 7.5% PLLA solution are very hard and tough. SEM observation shows that the pore structure of the matrix prepared from a 7.5% PLLA solution (FIGS. 2c and 2d) is almost the same as the matrix prepared from a 5.0% PLLA solution (FIGS. 14a and 14b), with a uniform distribution of HAP particles.

In general, matrices prepared from 5.0% and 7.5% PLLA solutions have a morphology slightly different from the matrix made from a 2.5% PLLA solution (FIGS. 1a and 1b). The pore structure is more uniform with pore size ranged from about 50 to 200 microns, and the pore walls are thicker than that of matrix from 2.5% PLLA solution. Comparing with the pore structure of a matrix from 5.0% PLLA solution, the pore size of the matrix derived from 7.5% PLLA solution is smaller and the walls of the pores are thicker.

4. Effect of Solvent on Pore Geometry

The solid-liquid phase separation is attributed to the crystallization of the solvent. When temperature of the polymer solution is lower than the freezing point (crystallization temperature) of the solvent, the crystallization of solvent takes place and polymer phase is expelled from the crystallization front as impurities. A continuous polymer rich phase is formed by aggregation of polymer expelled from every single solvent crystal. After solvent crystals have been sublimated, a matrix is formed with pores similar to the geometry of solvent crystals.

5. Effect of Inorganic Second Phase on Polymer/Inorganic Second Phase Matrix Pore Geometry When an inorganic compound is introduced into the polymer/solvent solution, the crystallization of solvent is disrupted by the solid inorganic second phase. While an understanding of the precise mechanism is not necessary to the successful us of the present invention, it is believed that the randomly distributed inorganic second phase particles change the solvent crystallization front by impeding the crystal growth and makes the crystals of the solvent irregular. Both polymer and inorganic second phase particles are expelled from the crystallization front, and form a polymer/inorganic second phase rich phase. After sublimation of solvent, this polymer/inorganic second phase rich phase forms a continuous skeleton for the polymer/inorganic second phase matrix, and the spaces taken by solvent crystals become pores of the matrix. As a result of irregular solvent crystal growth, the pores become irregular (more isotropic), and no channel structure or repeating partitions are observed.

Additional evidence of the effect of inorganic second phase on the structure of polymer/inorganic second phase matrices is demonstrated by varying the amount of inorganic compound in the polymer/inorganic second phase matrices while the polymer concentration is kept constant. Scanning Electron Micrographic (SEM) observation demonstrates the micropore structure of the matrix changes considerably with inorganic compound content. When inorganic second phase content is low, regular channels and ladder-like structures similar to those in a inorganic second phase free polymer matrix are observed (FIGS. 3a and 3b). With increasing inorganic second phase content, the pore structure becomes increasingly irregular. When inorganic second phase content is higher than 50wt%, the channels and ladder-like structure disappear (FIGS. 3c and 3d). These results demonstrate that pore structure of the polymer matrix can be modified by the incorporation of inorganic second phase.

6. Determinants of Porosity and Density in Polymer/Inorganic Second Phase Matrices As a general observation the density of polymer/inorganic second phase matrices, prepared by the above referenced solid-liquid phase separation and subsequent solvent sublimation, increases with polymer concentration and inorganic second phase contents. In parallel, porosity decreases with increasing polymer concentration and inorganic second phase content. Phase separation temperature does not show obvious effects on the porosity (density) of the polymer/inorganic second phase matrices in the composition range studied. For example, the densities of PLGA/HAP matrices are slightly higher than that of PLLA/HAP matrices prepared from the same polymer concentration, HAP content and processing conditions. Table 1 presents data relating the densities and porosities of PLLA/HAP and PLGA/HAP matrices prepared from PLLA/HAP/Dioxane and PLGA/HAP/Dioxane mixtures. Consistent with the above referenced general trends.

7. Effect of Quenching on Matrix Morphology

In the preparation of polymer matrix by solid-liquid phase separation from polymer solution, quenching temperature (cooling rate) is another effective tool in controlling the morphology of the matrix.

The crystallization process includes two stages: nucleation and growth. Generally, a high degree of supercooling (lower temperature) induces a high nucleation rate and a low crystal growth rate, which leads to the formation of large number of small crystals. In contrast, a relatively lower degree of supercooling (high temperature) induces a low nucleation rate and a high crystal growth rate, which leads to a small number of large crystals.

While it is not intended the instant invention be limited to a particular example, the following reaction is exemplar of the effect of quenching on matrix morphology. The freezing point of dioxane is about 12° C. When the temperature of a PLLA/HAP/dioxane mixture is lower than this temperature, crystallization of dioxane takes place. FIGS. 4a and 4b show the SEM micrographs of PLLA/HAP matrix formed by quenching the mixture to 8° C., which is slightly lower than the freezing point of dioxane.

At this temperature Dioxane is marginally supercooled. This quenching condition favors a low rate of nucleation but a relatively accelerated crystalline growth rate which gives rise to large solvent crystal formation, and thereby a PLLA/HAP matrix with a pore size up to 600 microns. When the PLLA/HAP/dioxane mixture is quenched with liquid nitrogen, the microstructure of the matrix formed is much different from that of the matrix prepared at higher temperatures (FIGS. 4c and 4d).

TABLE 1

| Polymer Concentration | Composition | Quenching Temperature(° C.) | Density g/cm$^3$ | Porosity |
|---|---|---|---|---|
| 2.5 (wt/V)% | PLLA/HAP = 100/0 | −18 | 0.045 | 94.8% |
| 2.5 (wt/v)% | PLLA/HAP = 90/10 | −18 | 0.049 | 93.4% |
| 2.5 (wt/v)% | PLLA/HAP = 70/30 | −18 | 0.060 | 92.5% |
| 2.5 (wt/v)% | PLLA/HAP = 50/50 | −18 | 0.090 | 89.9% |
| 2.5 (wt/v)% | PLLA/HAP = 10/90 | −18 | 0.120 | 85.1% |
| 5.0 (wt/v)% | PLLA/HAP = 100/0 | −18 | 0.083 | 92.7% |
| 5.0 (wt/v)% | PLLA/HAP = 90/10 | −18 | 0.086 | 91.7% |
| 5.0 (wt/v)% | PLLA/HAP = 70/30 | −18 | 0.110 | 91.0% |
| 5.0 (wt/v)% | PLLA/HAP = 50/50 | −18 | 0.144 | 89.2% |
| 5.0 (wt/v)% | PLLA/HAP = 30/70 | −18 | 0.203 | 86.6% |
| 2.5 (wt/v)% | PLLA/HAP = 100/0 | Liquid Nitrogen | 0.043 | 92.5% |
| 2.5 (wt/v)% | PLLA/HAP = 50/50 | Liquid Nitrogen | 0.085 | 88.0% |
| 2.5 (wt/v)% | PLLA/HAP = 100/0 | 8 | 0.047 | 95.6% |
| 2.5 (wt/v)% | PLLA/HAP = 50/50 | 8 | 0.090 | 90.9% |
| 2.5 (wt/v)% | PLGA/HAP = 50/50 | −18 | 0.126 | 87.5% |
| 5.0 (wt/v)% | PLGA/HAP = 50/50 | −18 | 0.151 | 85.7% |

B. Matrix Incubation in Simulated Body Fluid

1. Simulated Body Fluid

Human body fluid is supersaturated with apatite under normal conditions. W. Neuman and M. Neuman, in: The Chemical Dynamics of Bone Mineral (University of Chicago, Chicago, 1958) p.34. In this supersaturated environment, once a "seeding" apatite nuclei is formed on the surface of a inorganic second phase, apatite can spontaneously plate onto the surface of a matrix by consuming the calcium and phosphate ions from surrounding body fluid. This is significant because, in the case of an artificial material designed to bond with bone, it is essential that a bone-like apatite be first plated onto the surfaces of said material. Kokubo, et al., "Solutions able to reproduce in vivo surface-structure changes in bioactve ceramic A-W$^3$." *Journal of Biomedical Materials Research,* 24:721–732 (1990).

Simulated Body Fluid (SBF) provides a source for the constituents of carbonated bone-like apatite. Simulated body fluid (SBF) is used as an in vitro model to study calcium phosphate (apatite) formation or precipitation on the surfaces of different types of biomaterials. Kokubo, T., Ito, S., Huang, T., et al. Ca, P-rich layer formed on high-strength bioactive glass ceramic A-W. *J Biomed. Mater. Res.,* 1900, 24, 331–343., Li, P., Te, X., Kangasniemi, T., de Blieck-Hogervorst, J., Klein, C. and de Groot, K., In vivo calcium phosphate formation induced by sol-gel-prepared silica. *J Biomed Mater. Res.,* 1995, 29, 325–328., Li, P., Ohtsuki, C., Kokubo, T. et al., Apatite formation induced by silica gel in a simulated body fluid. *J Am. Ceram. Soc.,* 1992, 75, 2094–2097.

When X-ray diffractometry and infrared spectrophotometry are used to characterize the precipitates from SBF, they have indicated the formation of apatite. Abe et al.report that apatite was precipitated from SBFs onto the surface of different kinds of inert materials, e.g., metals, polymers and ceramics, without any chemical interactions between the precipitates and the substrate materials. Abe, Y., Kokubo and Yamamuro, T., Apatite coating on ceramics, metals and polymers utilizing a biological process. *J Mater Sci.: Mater. Med.,* 1990, 1, 233–238. Silica gel or titania gel materials can induce apatite formation on their surfaces in SBF.

Apatite precipitation has also been used as an indicator for the in vitro evaluation of the calcium-binding properties of different surfaces or structure-modified polymeric biomaterials. Calcium phosphate precipitates on a material from SBF are thus used in practice as an indication of potential bone apposition for biomaterials. Tretinnikov, O. N., Kato, K. and Ikada, Y., In vitro hydroxyapatite deposition onto a film surface-grafted with organophosphate polymer. *J. Biomed Mater. Res.,* 1994, 28, 1365–1373., Wan, C. A., Khor, E., Wong, J. M. and Hastings, G. W., Promotion of calcification on carboxymethylchitin discs. *Biomaterials,* 1996, 17, 1529–1534.

In the instant invention an SBF is prepared by dissolving reagent grade chemicals of NaCl, $NaHCO_3$, KCl, $K_2HPO_4 3H_2O$, $MgCl_2 6H_2O$, $CaCl_2$ and $Na_2SO_4$ in deionized water. While the inorganic ion concentration ($Na^+ 213$, $K^+ 7.5$, $Mg^{2+} 2.3$, $Ca^{2+} 3.8$, $Cl^- 223$, $HCO_3^- 27$, $HPO_4^{2-} 1.5$, $SO_4^{2-} 0.8$ in mM) of the instant example is 1.5 times those of human blood plasma, it is not intended the invention be limited to this value. Indeed, the preferred range of ion concentration is between 0.5 and 2.5 times the average values found in human plasma (FIG. 5), with a most preferred value in the range of 1.0 and 2.0 times said value for human plasma.

This SBF is buffered at a pH value of 7.4 at 37° C. with tris-(hydroxymethyl) aminomethane ($(CH_2OH)_3CNH_2$) and hydrochloric acid (HCl). The solution is metastable and does not precipitate calcium phosphate without external stimulation. This is significant because, with regard to the instant invention, contacting a porous matrix with the SBF serves as sufficient stimuli to "seed" apatite nuclei onto the matrix. These apatite nuclei serve as initiation points for the in situ expansion of apatite micro-particles which bond onto the surface of a porous matrix.

The present invention, however, is not limited to the formula for the SBF presented above molar concentrations for other suitable fluids are presented in Table 2.

2. Bonding of Hydroxyapatite Onto Matrix Surfaces

While it is not intended the present invention be limited to polymer matrices, in one embodiment of the instant invention a PLLA matrix is immersed in the SBF at 37° C. to grow apatite. Specifically, rectangular PLLA matrix specimens with dimensions of 12 mm×8 mm×6 mm are immersed into 100 ml SBF in a glass bottle maintained at 37° C. A series of brief evacuation-repressurization cycles are performed to force the solution into the pores of the matrices. Cycling is continued until no air bubbles are seen emerging from the matrices. The SBF is renewed every other day.

After 30 days, a large number of microparticles with a diameter ranging from 0.5 to 2 microns form on the surface of the PLLA pore walls (FIG. 6). The particles are assembled with small flake-like pieces.

3. Analysis of SBF Hydroxyapatite Incorporated Into the Matrix

Energy-dispersive spectroscopy (EDS) reveal the elements of the incubated PLLA matrix as carbon, oxygen, calcium and phosphorus (FIG. 7). Carbon and oxygen could be from both PLLA and the particles, but calcium and phosphorus could only be contributed by the bone-like carbonated apatite particles. These results confirm the similarity of the particles formed in the PLLA matrices to hydroxyapatite found in native bone.

Figure 8:
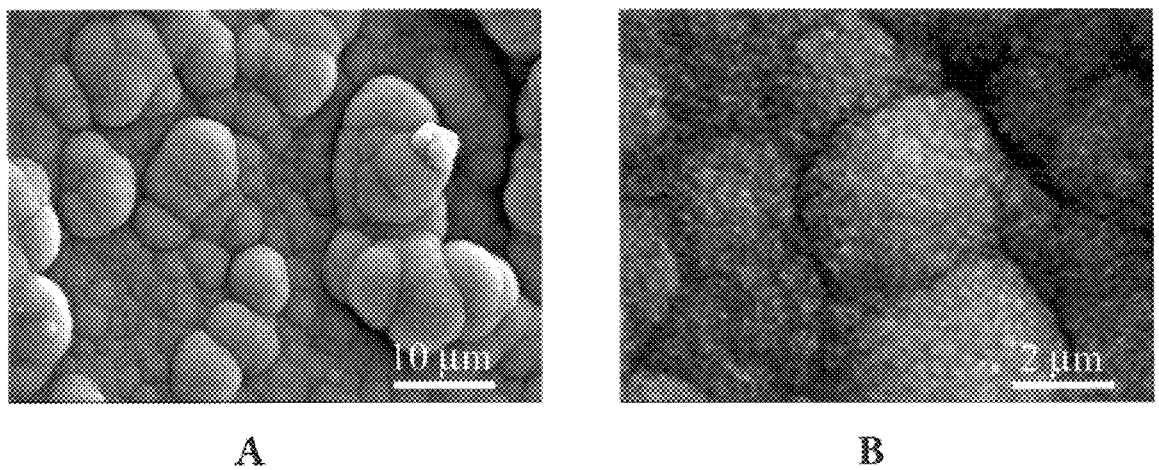
FIG. 8 presents SEMs, at different magnifications, of a PLLA film incubated in SBF for 15 days at different magnifications: (a) 2,000× and (b)10,000 ×.

Microparticles are also formed on solid PLLA films treated in SBF under the same conditions. The particles on the PLLA films are larger than in the PLLA matrices. The surfaces of the films are covered completely with the microparticles after 15 days of incubation (FIG. 8a). The morphology of the formed particles are also a flake-like assembly (FIG. 8b). EDS analysis indicates that calcium and phosphorus are also the main elements in the particles (FIG. 7).

Figure 9:
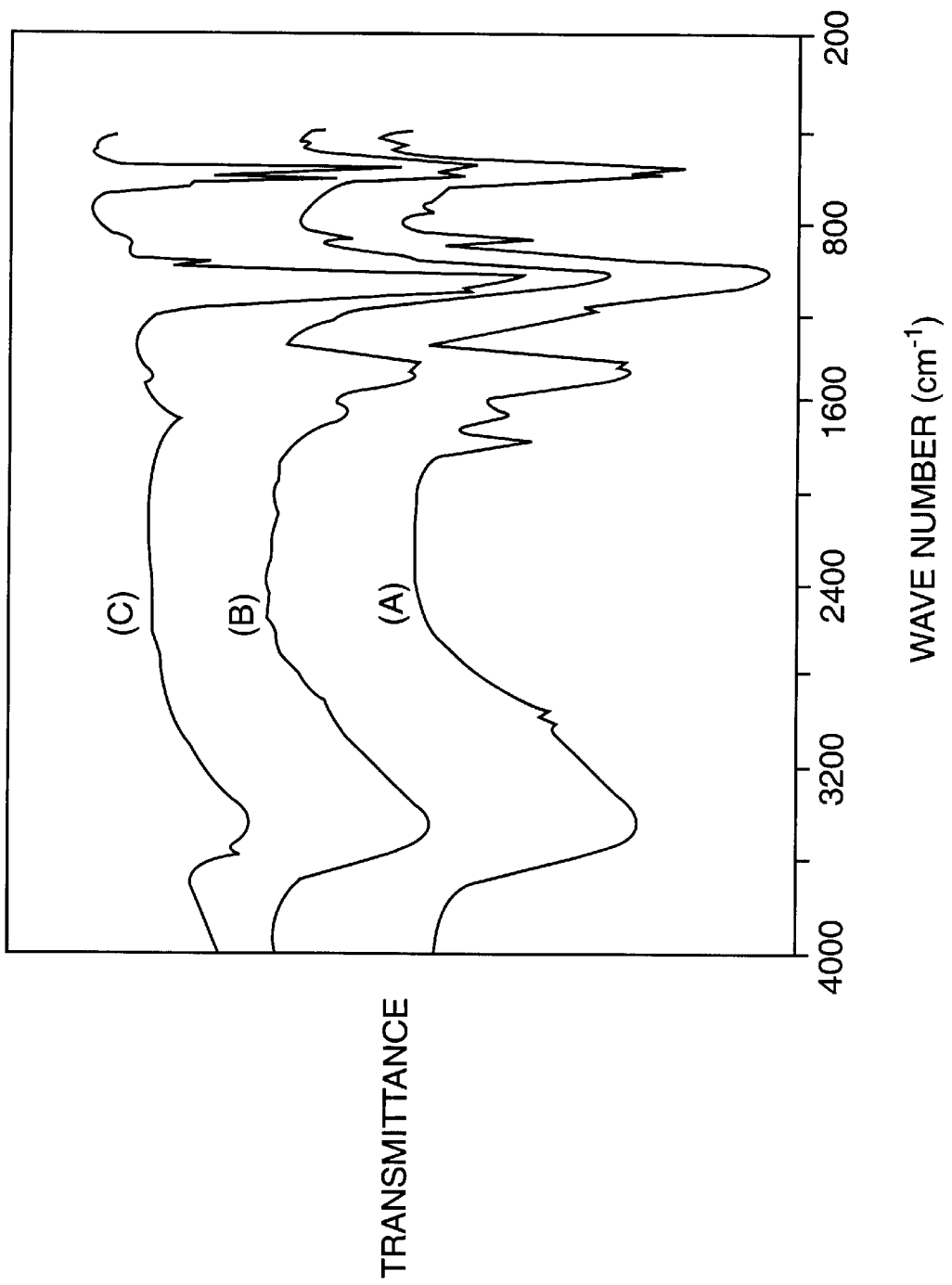
FIG. 9 presents a Fourier Transform Infrared (FTIR) spectra the apatite particles formed from SBF on: (a) PLLA film, (b) PLLA matrix, and a Fourier Transform Infrared (FTIR) spectra of (c) commercially available HAP.

IR spectroscopy reveals additional information on the microparticles formed in the PLLA matrices and on the PLLA films. The spectra of the formed particles are similar to that of a commercial synthetic hydroxyapatite (FIG. 9). The characteristic absorption bands of phosphate in HAP appearing at 565 $cm^{-1}$, 604 $cm^{-1}$, 962 $cm^{-1}$ and 1085 cm–1, which reflect phosphate vibration mode of $n_4$, $n_1$, and $n_3$ respectively, is observed for all three samples. The spectra of the formed particles has a strong absorption band at 873 $cm^{-1}$ corresponding to $n_2$ vibration mode of carbonate. The broad peak around 1640 $cm^{-1}$ is assigned to $n_3$ band of carbonate. These carbonate peaks from particles formed from SBF incubation are much higher than those in commercial synthetic HAP. Hydroxyl stretch is observed at 3570 $cm^{-1}$ in the spectrum of commercial synthetic hydroxyapatite. However, no evident peak at the same wavenumber is observed for the particles formed from SBF incubation. The large decrease of the hydroxyl stretch band intensity and the

TABLE 2

| | Concentrations (mM) | | | | | | | | |
|---|---|---|---|---|---|---|---|---|---|
| Solution | Na | K⁻ | $Mg^{2-}$ | $Ca^{2+}$ | $Cl^-$ | $HCO_3^-$ | $HPO_4^2$ | Buffer | pH |
| No. 1 | 142 | 5.0 | 0 | 1.6 | 144.0 | 4.2 | 1.0 | A | 7.25 |
| No. 2 | 142 | 5.0 | 0.7 | 1.6 | 145.4 | 4.2 | 1.0 | A | 7.25 |
| No. 3 | 142 | 5.0 | 1.5 | 2.5 | 148.8 | 4.2 | 1.0 | A | 7.25 |

Buffer A: $(CH_2OH)_3CNH_2$ 50 mM, HCl 45 mM.

strong carbonate bands of the precipitates from SBF indicated the carbonate substitution for OH in hydroxyapatite. These results suggest that the particles in a PLLA matrix or on a PLLA film from SBF incubation are carbonated apatite, which are similar in composition and structure to the natural apatite in human and animal hard tissues. The peaks at 1455 cm$^{-1}$ ((CH$_3$), 1759cm$^{-1}$ (nC=O) and peaks ranging from 2870 to 3000 cm$^{-1}$ (nC—H) in the spectrum are attributed to the PLLA, which could be scratched with the apatite particles into the KBr film prepared for IR analysis. This is also an indication that there is a strong adhesion between the apatite particles and the PLLA.

Figures 11A, 11B:
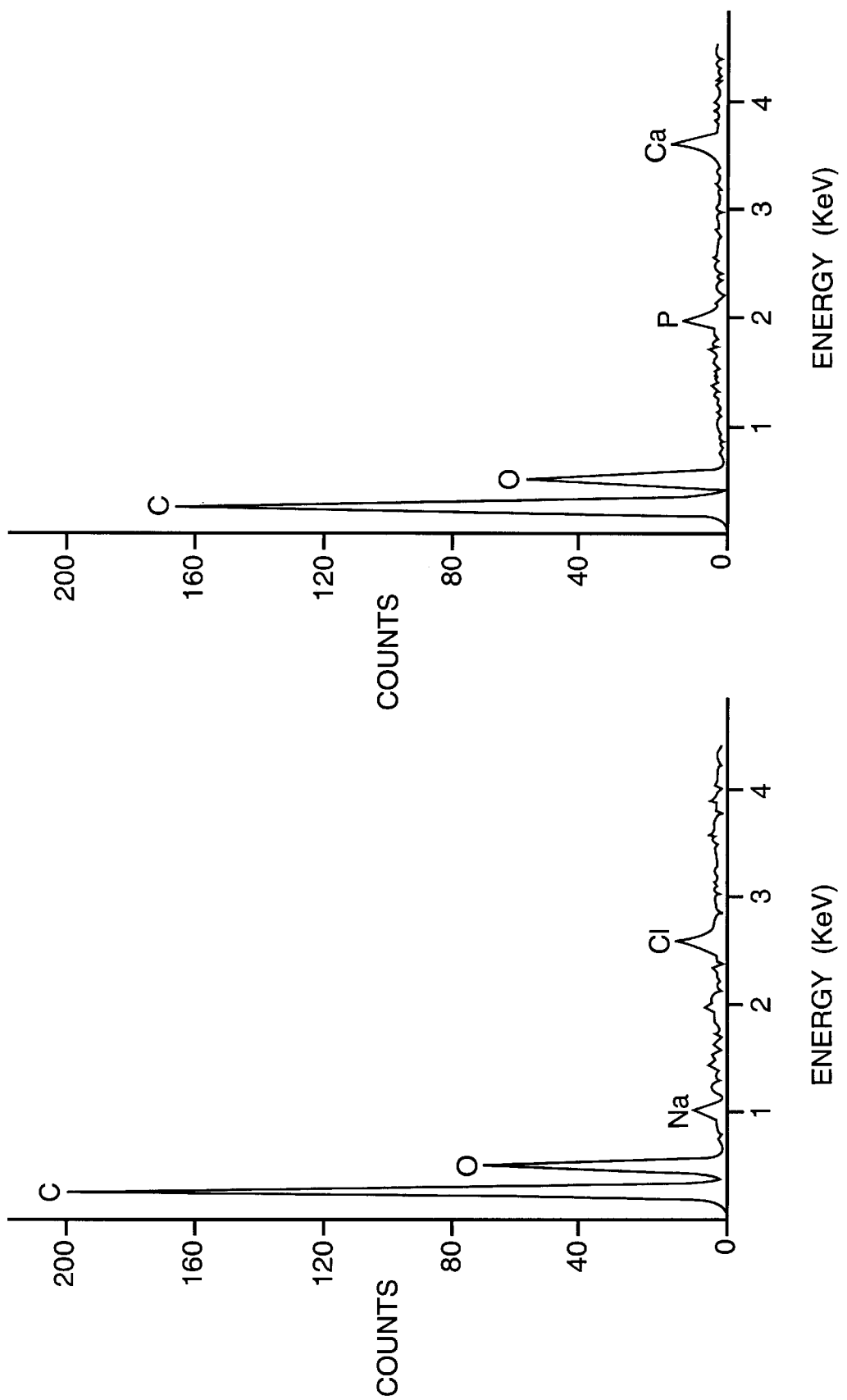
FIG. 11 presents an (EDS) of a PLLA matrix incubated in SBF for different periods of time: (a) 3 days, (b) 6 days, and (c) 15 days.

The variation of the particle number and size in the PLLA matrices is achieved by varying the incubation time in the SBF (FIG. 10). Both number and size of the apatite particles increased with incubation time. Almost no apatite microparticles are observed on the surfaces of the PLLA pore walls after 3 days of incubation. Scattered and small microparticles are observed after 6 days of incubation. After 15 days of incubation, a large number of apatite microparticles with relative bigger particle size are observed. EDS analysis also demonstrates the calcium and phosphate contents increase with incubation time (FIG. 11). As a consequence of particle growth from the nuclei formed at different times, there is a wide size distribution.

4. Factors Regulating Apatite Nucleation on Matrices

Figure 12:
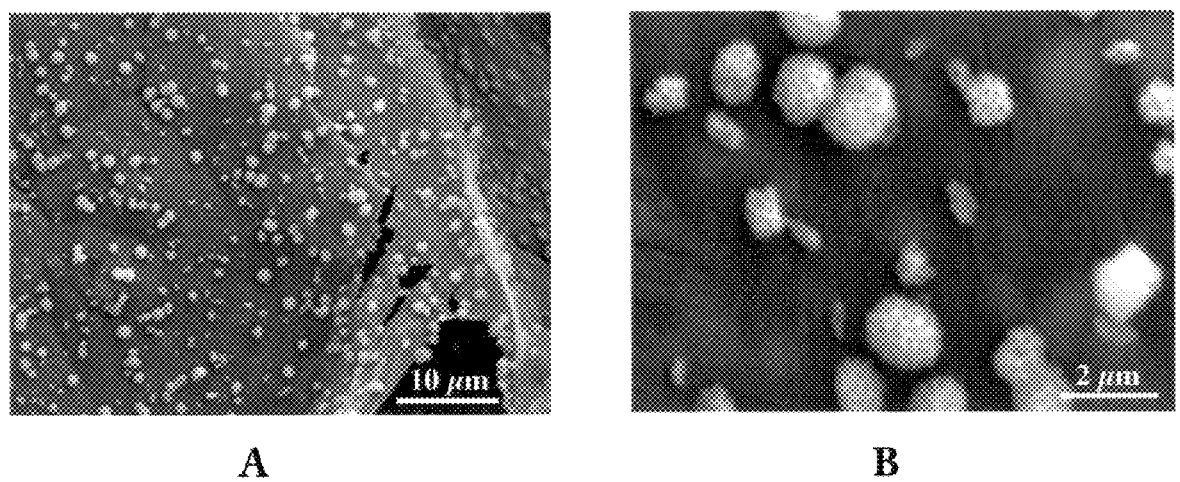
FIG. 12 presents SEMs of a PLLA matrix incubated in SBF for 30 days, where the SBF was not renewed after 15 days of incubation, at different magnifications: (a) 2,000× and (b) 10,000×.

FIGS. 12a and 12b are the SEM micrographs of a PLLA matrix with a 30-day incubation but no SBF change after the 15 days. The particle number is almost the same as that from 30 days of incubation with regular SBF change. The number of large apatite particles is smaller than that with regular SBF change. Additionally, the average particle size is smaller than particles found in matrices grown for 30 days with regular SBF changes. These results confirm that incubation time is important for the apatite nucleation and the ion concentration in SBF is important for apatite particle growth.

In order to evaluate the effect of polymer hydration on apatite nucleation, several PLLA matrix samples are immersed in distilled water at 37° C. for 15 days before incubation in SBF. The number of apatite particles formed in the water treated PLLA matrices (FIGS. 13a and 13b) are much larger than that in the PLLA matrices without water treatment (FIG. 10d) for the same SBF incubation time. The hydrated groups such as COOH and OH from the PLLA hydrolysis may contribute to the higher apatite nucleation rate in the water treated PLLA matrices. This result indicated that the hydrolysis of PLLA may have been playing an important role during the apatite formation in the PLLA matrices.

C. Cell Cultivation and Incorporation into Polymer/Inorganic Second Phase Matrices MC3T3-E1 osteoblasts are cultured and expanded in tissue culture medium (89% DMEM containing 4500 mg/L D-glucose, 10% FBS, 1% P/S). The cultured cells are trypsinized with trypsin-EDTA and is washed twice with DPBS. The cells are then suspended in "complete medium" (89% DMEM, 10% FBS, 1% P/S, and 50 mg/L-ascorbic acid) at a density of $1 \times 10^7$ cells/ml. Circular discs with a diameter of 10 mm and a thickness of 1.5 mm are cut from the above composite matrix and one disc is fit in each well of a customer-made twelve-well Teflon culture plate. $1.5 \times 10^6$ cells in total of 0.5 ml complete medium are added to each of the matrix discs. They are cultured in a humidified incubator at 37° C. in the presence of 5% CO$_2$. The medium (0.5 ml each) is changed daily. Two weeks later, cell infiltrated matrix is fixed in 10% neutral buffered formalin, embedded in paraffin, and cut into 5 µm cross sections for histological analysis. The osteoblasts are normal in appearance, having laid down some extracellular matrix, and penetrating into the porous polymer/inorganic second phase matrix.

III. Preferred Embodiments

In one embodiment, a porous composite PLLA/HAP matrix from a dioxane solution is synthesized. Specifically, 1.0 gram poly(L-lactic acid) (PLLA) is added into a flask containing 20 ml dioxane to make a 5% (wt/v%) solution at 50° C. 1.0 gram hydroxyapatite (HAP) is then added into the solution to make a PLLA/HAP/dioxane mixture. 10 ml of the prepared mixture is transferred into a beaker (30 ml). The beaker containing the mixture is then rapidly transferred into a freezer at −18° C. to solidify the solvent and induce solid-liquid phase separation. The solidified mixture is maintained at that temperature for 2 hours and then is immersed into liquid nitrogen to deep freeze the mixture. The frozen mixture is transferred into a freeze-drying vessel at −5° C. to −10° C. in an ice/salt bath. The sample is freeze-dried at 0.5 mmHg for four days to completely remove the solvent. The density and porosity of the composite matrix are measured by liquid displacement to be 0.083 g/cm$^3$ and 92.7% respectively. The porous microstructure of the matrix is observed with SEM (FIGS. 14a and 14b).

In another embodiment, a porous composite PLGA/HAP matrix from a dioxane solution is synthesized. Specifically, 0.5 gram poly(D,L-lactic acid-co-glycolic acid (75/25)) (PLGA75/25) is added into a flask containing 20 ml dioxane to make a 2.5% solution at 50° C. 0.5 gram HAP is then added into the solution to make a PLGA/HAP/dioxane mixture. 10 ml of the prepared mixture is transferred into a beaker (30 ml). The beaker containing the mixture is then rapidly transferred into a freezer at −18° C. to solidify the solvent and induce solid-liquid phase separation. The solidified mixture is maintained at that temperature for 2 hours and then is immersed into liquid nitrogen to deep freeze the mixture. The frozen mixture is transferred into a freeze-drying vessel at −5° C. to −10° C. in an ice/salt bath. The sample is freeze-dried at 0.5 mmHg for four days to completely remove the solvent. The density and porosity of the composite matrix are 0.126 g/cm$^3$ and 87.5% respectively. The porous microstructure of the matrix is observed with SEM (FIGS. 15a and 15b).

In another embodiment, a porous composite PLLA/HAP matrix from a dioxane/H$_2$O solution is synthesized. Specifically, 1.0 gram PLLA is added into a flask containing 20 ml dioxane/H$_2$O(90/10) to make a 5% solution at 50° C. 1.0 gram HAP is then added into the solution to make a PLLA/HAP/dioxane/H$_2$O mixture. 10 ml of the prepared mixture is transferred into a beaker (30 ml). The beaker containing the mixture is then rapidly transferred into a freezer at −18° C. to solidify the solvent and induce solid-liquid phase separation. The solidified mixture is maintained at that temperature for 2 hours and then is immersed into liquid nitrogen to deep freeze the mixture. The frozen mixture is transferred into a freeze-drying vessel at −5° C. to −10 C. in an ice/salt bath. The sample is freeze-dried at 0.5 mmHg for four days to completely remove the solvent. The density and porosity of the composite matrix are 0.162 g/cm$^3$ and 88.8% respectively. The porous microstructure of the matrix are observed with SEM (FIGS. 16a and 16b).

In another embodiment, a porous composite PLLA/HAP matrix from a benzene solution is synthesized. Specifically, 1.0 gram PLLA is added into a flask containing 20 ml benzene to make a 5% solution at 50° C. 1.0 gram HAP is then added into the solution to make a PLLA/HAP/benzene mixture. 10 ml of the prepared mixture is transferred into a beaker (30 ml). The beaker containing the mixture is then rapidly transferred into a freezer at −18° C. to solidify the solvent and induce solid-liquid phase separation. The solidified mixture is maintained at that temperature for 2 hours and then is immersed into liquid nitrogen to deep freeze the mixture. The frozen mixture is transferred into a freeze-drying vessel at −5° C. to −10° C. in an ice/salt bath. The sample is freeze-dried at 0.5 mmHg for four days to completely remove the solvent. The density and porosity of the composite matrix are 0. 163 g/cm$^3$ and 91.1% respectively. The porous microstructure of the matrix is observed with SEM (FIG. 17).

In another embodiment, a porous composite PLGA/HAP matrix from a benzene solution is synthesized. Specifically, 1.0 gram PLGA75/25 is added into a flask containing 20 ml benzene to make a 5% solution at 50° C. 1.0 gram HAP is then added into the solution to make a PLGA/HAP/benzene mixture. 10 ml of the prepared mixture is transferred into a beaker (30 ml). The beaker containing the mixture is then rapidly transferred into a freezer at −18° C. to solidify the solvent and induce solid-liquid phase separation. The solidified mixture is maintained at that temperature for 2 hours and then is immersed into liquid nitrogen to deep freeze the mixture. The frozen mixture is transferred into a freeze-drying vessel at −5° C. to −10° C. in an ice/salt bath. The sample is freeze-dried at 0.5 mmHg for four days to completely remove the solvent. The density and porosity of the composite matrix are 0.131 g/cm$^3$ and 93.9% respectively. The porous microstructure of the matrix is observed with SEM (FIG. 18).

In another embodiment, a porous composite PLLA/HAP matrix from a benzene/chloroform (90/10) solution is synthesized. Specifically, 1.0 gram PLLA is added into a flask containing 20 ml benzene/chloroform (90/10) to make a 5% solution at 50° C. 1.0 gram HAP is then added into the solution to make a PLLA/HAP/benzene/chloroform mixture. 10 ml of the prepared mixture is transferred into a beaker (30 ml). The beaker containing the mixture is then rapidly transferred into a freezer at −18° C. to solidify the solvent and induce solid-liquid phase separation. The solidified mixture is maintained at that temperature for 2 hours and then is immersed into liquid nitrogen to deep freeze the mixture. The frozen mixture is transferred into a freeze-drying vessel at −5° C. to −10C. in an ice/salt bath. The sample is freeze-dried at 0.5 mmHg for four days to completely remove the solvent. The density and porosity of the composite matrix are 0.123 g/cm$^3$ and 93.2% respectively. The porous microstructure of the matrix is observed with SEM (FIG. 19).

In another embodiment, a porous composite PMMA/HAP matrix from a dioxane solution is synthesized. Specifically, 1.0 gram poly(methyl methacrylate) (PMMA) is added into a flask containing 20 ml dioxane to make a 5% solution at 50° C. 1.0 gram HAP is then added into the solution to make a PMMA/HAP/dioxane mixture. 10 ml of the prepared mixture is transferred into a beaker (30 ml). The beaker containing the mixture is then rapidly transferred into a freezer at −18° C. to solidify the solvent and induce solid-liquid phase separation. The solidified mixture is maintained at that temperature for 2 hours and then is immersed into liquid nitrogen to deep freeze the mixture. The frozen mixture is transferred into a freeze-drying vessel at −5° C. to −10C. in an ice/salt bath. The sample is freeze-dried at 0.5 mmHg for four days to completely remove the solvent. The density and porosity of the composite matrix are 0.146 g/cm$^3$ and 87.5% respectively. The porous microstructure of the matrix is observed with SEM (FIG. 20).

In another embodiment, a porous composite PMMA-MAA/HAP matrix from a dioxane solution is synthesized. Specifically, 1.0 gram poly(methyl methacrylate-co-methacrylic acid (80/20)) (PMMA-MAA) is added into a flask containing 20 ml dioxane to make a 5% solution at 50° C. 1.0 gram HAP is then added into the solution to make a PMMA-MAA/HAP/dioxane mixture. 10 ml of the prepared mixture is transferred into a beaker (30 ml). The beaker containing the mixture is then rapidly transferred into a freezer at −18° C. to solidify the solvent and induce solid-liquid phase separation. The solidified mixture is maintained at that temperature for 2 hours and then is immersed into liquid nitrogen to deep freeze the mixture. The frozen mixture is transferred into a freeze-drying vessel at −5° C. to −10° C. in an ice/salt bath. The sample is freeze-dried at 0.5 mmHg for four days to completely remove the solvent. The density and porosity of the composite matrix are 0.138 g/cm$^3$ and 92.3% respectively. The porous microstructure of the matrix is observed with SEM (FIG. 21).

In another embodiment, a porous composite PS/HAP matrix from a dioxane solution is synthesized. Specifically, 1.0 gram polystyrene (PS) is added into a flask containing 20 ml dioxane to make a 5% solution at 50° C. 1.0 gram HAP is then added into the solution to make a PS/HAP/dioxane mixture. 10 ml of the prepared mixture is transferred into a beaker (30 ml). The beaker containing the mixture is then rapidly transferred into a freezer at −18° C. to solidify the solvent and induce solid-liquid phase separation. The solidified mixture is maintained at that temperature for 2 hours and then is immersed into liquid nitrogen to deep freeze the mixture. The frozen mixture is transferred into a freeze-drying vessel at −5° C. to −10° C. in an ice/salt bath. The sample is freeze-dried at 0.5 mmHg for four days to completely remove the solvent. The density and porosity of the composite matrix are 0.137 g/cm$^3$ and 93.2% respectively. The porous microstructure of the matrix are observed with SEM (FIG. 22).

In another embodiment, a porous composite PLLA/CAP matrix from a dioxane solution is synthesized. Specifically, 1.0 gram poly(L-lactic acid) (PLLA) is added into a flask containing 20 ml dioxane to make a 5% (wt/v%) solution at 50° C. 1.0 gram calcium phosphate (CAP) is then added into the solution to make a PLLA/CAP/dioxane mixture. 10 ml of the prepared mixture is transferred into a beaker (30 ml). The beaker containing the mixture is then rapidly transferred into a freezer at −18° C. to solidify the solvent and induce solid-liquid phase separation. The solidified mixture is maintained at that temperature for 2 hours and then is immersed into liquid nitrogen to deep freeze the mixture. The frozen mixture is transferred into a freeze-drying vessel at −5° C. to −10° C. in an ice/salt bath. The sample is freeze-dried at 0.5 mmHg for four days to completely remove the solvent. The density and porosity of the composite matrix are measured by liquid displacement to be 0.155 g/cm$^3$ and 93.8% respectively. The porous microstructure of the matrix are observed with SEM (FIGS. 23a and 23b).

In another embodiment, a porous composite PLLA/GP matrix from a dioxane solution is synthesized. Specifically, 1.0 gram poly(L-lactic acid) (PLLA) is added into a flask containing 20 ml dioxane to make a 5% (wt/v%) solution at 50° C. 1.0 gram glass powder (SiO.Al$_2$O$_3$.CaF$_2$) (GP) is then added into the solution to make a PLLA/GP/dioxane mixture. 10 ml of the prepared mixture is transferred into a beaker (30 ml). The beaker containing the mixture is then rapidly transferred into a freezer at −18° C. to solidify the solvent and induce solid-liquid phase separation. The solidified mixture is maintained at that temperature for 2 hours and then is immersed into liquid nitrogen to deep freeze the mixture. The frozen mixture is transferred into a freeze-drying vessel at −5° C. to −10°C. in an ice/salt bath. The sample is freeze-dried at 0.5 mmHg for four days to completely remove the solvent. The density and porosity of the composite matrix are measured by liquid displacement to be 0.157 g/cm$^3$ and 90.3% respectively. The porous microstructure of the matrix are observed with SEM (FIGS. 24a and 24b).

We claim:

1. A method, comprising:
   a) providing:
      i) a polymer source,
      ii) an inorganic compound, and
      iii) a solvent solution having a freezing temperature below room temperature;
   b) mixing said polymer with said solvent solution to create a polymer solution above room temperature;
   c) adding said inorganic compound to said polymer solution to create a mixture in a container;
   d) placing said container at a temperature below said freezing temperature of said solvent solution so as to create a solidified matrix; and
   e) treating said solidified matrix under conditions whereby a solvent free matrix is created having a porosity greater than approximately 80%.

2. The method of claim 1, wherein said porosity is greater than approximately 85%.

3. The method of claim 1, wherein said porosity is greater than approximately 90%.

4. The method of claim 1, wherein said porosity is approximately 95%.

5. The method of claim 1, wherein said polymer source is selected from the group consisting of poly(L-lactic acid), poly(D,L-lactic acid-co-glycolic acid (PLGA), poly(methyl methacrylate) and polystyrene.

6. The method of claim 1, wherein said inorganic compound is selected from the group consisting of hydroxyapatite, calcium phosphate and glass powder.

7. The method of claim 1, wherein said solvent solution comprises a solvent selected from the group consisting of dioxane, benzene and chloroform.

8. The method of claim 1, wherein said solvent solution comprises a mixture of dioxane and water.

9. The method of claim 1, wherein said solvent solution comprises a mixture of benzene and chloroform.

10. A method, comprising:
    a) providing:
       i) a polymer source,
       ii) an inorganic compound, and
       iii) a solvent solution comprising dioxane;
    b) mixing said polymer with said solvent to create a polymer solution;
    c) adding said inorganic compound to said polymer solution to create a mixture in a container;
    d) placing said container at a temperature below dioxane's melting point; and
    e) freezing said solvent in said mixture to create a frozen mixture;
    f) treating said frozen mixture under conditions whereby a solvent free matrix is created having a porosity greater than approximately 80%.

11. The method of claim 10, wherein said treating of step f) comprises drying to remove said solvent.

12. The method of claim 10, wherein said porosity is greater than approximately 85%.

13. The method of claim 10, wherein said porosity is greater than approximately 90%.

14. The method of claim 10, wherein said porosity is approximately 95%.

15. The method of claim 10, wherein said polymer source is selected from the group consisting of poly(L-lactic acid), poly(D,L-lactic acid-co-glycolic acid (PLGA), poly(methyl methacrylate) and polystyrene.

16. The method of claim 10, wherein said inorganic compound is selected from the group consisting of hydroxyapatite, calcium phosphate and glass powder.

17. The method of claim 10, wherein said solvent solution consists of dioxane.

18. The method of claim 10, wherein said solvent solution comprises a mixture of dioxane and water.

19. A method, comprising:
    a) providing:
       i) a polymer source,
       ii) a solvent, and
       iii) a simulated body fluid;
    b) mixing said polymer with said solvent to create a homogenous polymer solution;
    c) subjecting said mixture to such conditions whereby a solvent free matrix is created;
    d) contacting said solvent free matrix with said simulated body fluid.

20. A method, comprising:
    a) providing:
       i) a polymer source,
       ii) an inorganic compound, and
       iii) a solvent solution comprising benzene;
    b) mixing said polymer with said solvent solution to create a polymer solution;
    c) adding said inorganic compound to said polymer solution to create a mixture in a container;
    d) placing said container at a temperature below benzene's melting point so as to create a solidified matrix; and
    e) treating said mixture under conditions whereby a solvent free matrix is created having porosity greater than approximately 80%.

21. The method of claim 20, wherein said polymer source is selected from the group consisting of poly(L-lactic acid), poly (D,L-lactic acid-co-glycolic acid (PPGA), poly(methyl methacrylate) and polystyrene.

* * * * *